United States Patent [19]

Ordahl et al.

[11] Patent Number: 5,776,776
[45] Date of Patent: Jul. 7, 1998

[54] DTEF-1 ISOFORMS AND USES THEREOF

[75] Inventors: Charles P. Ordahl; Anthony Azakie; Sarah B. Larkin. all of San Francisco; Iain K. G. Farrance. El Cerrito, all of Calif.

[73] Assignee: The Regents of the University of California. Oakland, Calif.

[21] Appl. No.: 615,170

[22] Filed: Mar. 12, 1996

Related U.S. Application Data

[63] Continuation-in-part of Ser. No. 191,493, Feb. 4, 1994, abandoned.
[51] Int. Cl.$^6$ .............................. C12N 5/10; C12N 1/00; C12N 15/12; C12N 15/63
[52] U.S. Cl. ...................... 435/366; 435/243; 435/320.1; 435/325; 536/23.5
[58] Field of Search .................... 536/23.5, 23.1; 435/325, 410, 243, 366, 320.1

[56] References Cited

PUBLICATIONS

Xiao et al. Cell, May 17, 1991, vol. 65 : pp. 551–568.
Ngo et al. The Protein Folding Problem and Tertiary Structure Prediction, 1994, Mertz et al (Eds), Birkhauser, Boston, MA, pp. 433 and 492–495.

*Primary Examiner*—George C. Elliott
*Assistant Examiner*—Terry A. McKelvey
*Attorney, Agent, or Firm*—Townsend and Townsend and Crew LLP

[57] ABSTRACT

Transcription enhancer factor 1 (TEF-1) gene family polypeptides are described. In particular, DTEF-1 isoforms are provided. The isoforms may be used for the differential regulation of genes which contain upstream TEF-1 binding sites. Thus, TEF-1 family polypeptides may be used to directly or indirectly regulate transcription of genes linked to the TEF-1 binding sites, such as genes which are expressed in cardiac tissue.

5 Claims, 17 Drawing Sheets

FIG. 1(a)

```
          10         20         30         40         50         60         70
          *          *          *          *          *          *          *
TCATACCAAC TCTCATTCCA CGCGTTCCTC GTTTACTCCT TTAAAACTCC AGGGAAAATA AAAACCCTCT 80         90        100        110        120        130        140
          *          *          *          *          *          *          *
CTTTTCTTCC CAAATTCTGG CGGAACTGGC CTCCCCCCGC CGCCGTGCAG TCTCGCCGTC CGGCCCGCCG 150        160        170        180        190        200
              *          *          *          *          *          *
CTCCGTACTC TTCAGGTTCT GAGTCTGCTT CTCCACGTGG CACC TTG GAG CTT CTA GCT GGC ACC
                                                 L   E   L   L   A   G   T
```

```
    210        220        230        240        250        260
    *          *          *          *          *          *
ATT ACC TCC GAG TGG AGC TCT CCT GCC TCC CCT GAG GGG AGC AAC GAT TCA GGG GGC
 I   T   S   E   W   S   S   P   A   S   P   E   G   S   N   D   S   G   G 270        280        290        300        310
    *          *          *          *          *
AGT GAG GCC TTG GAC AAA CCA ATT GAC AAT GAT GCT GAG GGT GTA TGG AGT CCA GAC
 S   E   A   L   D   K   P   I   D   N   D   A   E   G   V   W   S   P   D 320        330        340        350        360        370
*          *          *          *          *          *
ATT GAG CAG AGC TTC CAG GAA GCG CTA GCC ATC TAC CCA CCA TGT GGA CGG CGG AAG
 I   E   Q   S   F   Q   E   A   L   A   I   Y   P   P   C   G   R   R   K 380        390        400        410        420        430
    *          *          *          *          *          *
ATT ATC TTG TCA GAC GAA GGC AAG ATG TAT GGC CGA AAT GAG CTG ATT GCC CGT TAT
 I   I   L   S   D   E   G   K   M   Y   G   R   N   E   L   I   A   R   Y 440        450        460        470        480        490
    *          *          *          *          *          *
ATT AAG CTG AGA ACA GGG AAA ACA CGC ACA AGG AAA CAG GTA TCT AGT CAC ATC CAG
 I   K   L   R   T   G   K   T   R   T   R   K   Q   V   S   S   H   I   Q
```

FIG. 1(b)

```
           500         510         520         530         540
            *           *           *           *           *
    GTC CTG GCA AGG CGG AAA GCC AGA GAG ATC CAA GCC AAG CTC AAG GAC CAG ACA GCT
     V   L   A   R   R   K   A   R   E   I   Q   A   K   L   K   D   Q   T   A 550         560         570         580         590         600
    *           *           *           *           *           *
    AAA GAT AAA GCT ATG CAG AGT ATC GCT ACA ATG TCA TCT GCC CAG ATA ATC TCT GCA
     K   D   K   A   M   Q   S   I   A   T   M   S   S   A   Q   I   I   S   A 610         620         630         640         650         660
            *           *           *           *           *           *
    ACT GCC TTC CAT AGT AAA ATG GCC TTG CCA GGT CTC CCA CGA TCA GCC TAT CCT GCT
     T   A   F   H   S   K   M   A   L   P   G   L   P   R   S   A   Y   P   A 670         680         690         700         710
                  *           *           *           *           *
    GTT TCT GGG TTT TGG CAA GGA GCT TTG CCA GGC CAA GCT GGA TCT TCA CAA GAT GTG
     V   S   G   F   W   Q   G   A   L   P   G   Q   A   G   S   S   Q   D   V 720         730         740         750         760         770
    *           *           *           *           *           *
    AAA CCT TTT ACT CAA CAA CCC TAT GCT CTA CAG CCT TCA CTG CCA TTA CCA GGG TTT
     K   P   F   T   Q   Q   P   Y   A   L   Q   P   S   L   P   L   P   G   F 780         790         800         810         820         830
            *           *           *           *           *           *
    GAC TCT CCC ACT GGC CTC CCA CCT TCA TCA TCA ACA CCA GCT TGG CAA GGA CGA AGG
     D   S   P   T   G   L   P   P   S   S   S   T   P   A   W   Q   G   R   R 840         850         860         870         880
                  *           *           *           *           *
    GTT GCT AGC TCC AAA CTT TGG ATG TTA GAA TTC TCT GCA TTC TTG GAA CAA CAG CAA
     V   A   S   S   K   L   W   M   L   E   F   S   A   F   L   E   Q   Q   Q
```

FIG. 1(c)

```
      890         900         910         920         930         940
       *           *           *           *           *           *
GAT CAA GAC ACG TAT AAC AAA CAC CTG TTT GTG CAC ATC GGG CAG TCA AAT CCC AGC
 D   Q   D   T   Y   N   K   H   L   F   V   H   I   G   Q   S   N   P   S 950         960         970         980         990        1000
       *           *           *           *           *           *
TAC AGT GAT CCC TAC CTT GAG GCA GTG GAT ATC CGA CAA ATC TAT GAC AAG TTC CCT
 Y   S   D   P   Y   L   E   A   V   D   I   R   Q   I   Y   D   K   F   P 1010        1020        1030        1040        1050        1060
       *           *           *           *           *           *
GAG AAA AAA GGG GGC CTG AAG GAG CTG TTT GAA AGG GGG CCA GCA AAT GCC TTC TTC
 E   K   K   G   G   L   K   E   L   F   E   R   G   P   A   N   A   F   F 1070        1080        1090        1100        1110
       *           *           *           *           *
CTC GTC AAA TTC TGG GCT GAT TTG AAC ACC AAT ATT GAA GAT GAA TCC AGA TCT TTC
 L   V   K   F   W   A   D   L   N   T   N   I   E   D   E   S   R   S   F 1120        1130        1140        1150        1160        1170
      *           *           *           *           *           *
TAT GGT GTT TCC AGT CAA TAT GAG AGC CCA GAA AAT ATG GTC ATT ACC TGT TCC ACT
 Y   G   V   S   S   Q   Y   E   S   P   E   N   M   V   I   T   C   S   T 1180        1190        1200        1210        1220        1230
       *           *           *           *           *           *
AAA GTG TGT TCC TTT GGA AAG CAG GTG GTG GAG AAA GTG GAG ACA GAG TAT GCA CAC
 K   V   C   S   F   G   K   Q   V   V   E   K   V   E   T   E   Y   A   H 1240        1250        1260        1270        1280
       *           *           *           *           *
TAT GAA AAT GGA CAC TAT GCC TAT CGC ATT CAT CGT TCT CCT CTC TGT GAA TAC ATG
 Y   E   N   G   H   Y   A   Y   R   I   H   R   S   P   L   C   E   Y   M
```

FIG. 1(d)

```
        1290        1300        1310        1320        1330        1340
         *           *           *           *           *           *
ATA AAC TTC ATT CAT AAA CTC AAG CAC CTT CCT GAG AAG TAC ATG ATG AAC AGT GTA
 I   N   F   I   H   K   L   K   H   L   P   E   K   Y   M   M   N   S   V 1350        1360        1370        1380        1390        1400
         *           *           *           *           *           *
CTG GAG AAC TTT ACT ATC TTA CAG GTT GTG ACA AAC AGG GAC ACA CAG GAG ACC TTG
 L   E   N   F   T   I   L   Q   V   V   T   N   R   D   T   Q   E   T   L 1410        1420        1430        1440        1450
         *           *           *           *           *
CTG TGC ATA GCA TAT GTT TTT GAG GTG TCA GCT AGT GAC CAT GGT GCC CAG CAT CAC
 L   C   I   A   Y   V   F   E   V   S   A   S   D   H   G   A   Q   H   H 1460        1470        1480        1490        1500        1510
    *           *           *           *           *           *
ATC TAC CGG CTG GTG AAG GAC TAG AGA CTA TCT GCC CTG AGT CAT CCA TGA GAT GCG
 I   Y   R   L   V   K   D   *   R   L   S   A   L   S   H   P   *   D   A 1520        1530        1540        1550        1560        1570
         *           *           *           *           *           *
TGT CTG AGG AAA AAG TCT GTG CTT GAA AAT CCC TTG ACT CTT TTC ACC AAA TTG AAA
 C   L   R   K   K   S   V   L   E   N   P   L   T   L   F   T   K   L   K 1580        1590        1600        1610        1620
         *           *           *           *           *
AAT AAA CCG CAG ATA CTG TGT ATT TTC AGA AAA GTA AAA AAA AAA AAA AAA AAA
 N   K   P   Q   I   L   C   I   F   R   K   V   K   K   K   K   K   K
```

FIG. 2(a)

```
         10         20         30         40         50         60         70
          *          *          *          *          *          *          *
TCATACCAAC TCTCATTCCA CGCGTTCCTC GTTTACTCCT TTAAAACTCC AGGGAAAATA AAAACCCTCT 80         90        100        110        120        130        140
          *          *          *          *          *          *          *
CTTTTCTTCC CAAATTCTGG CGGAACTGGC CTCCCCCCGC CGCCGTGCAG TCTCGCCGTC CGGCCCGCCG 150        160        170        180        190        200
          *          *          *          *          *          *
CTCCGTACTC TTCAGGTTCT GAGTCTGCTT CTCCACGTGG CACC TTG GAG CTT CTA GCT GGC ACC
                                                 L   E   L   L   A   G   T 210        220        230        240        250        260
          *          *          *          *          *          *
ATT ACC TCC GAG TGG AGC TCT CCT GCC TCC CCT GAG GGG AGC AAC GAT TCA GGG GGC
 I   T   S   E   W   S   S   P   A   S   P   E   G   S   N   D   S   G   G 270        280        290        300        310
          *          *          *          *          *
AGT GAG GCC TTG GAC AAA CCA ATT GAC AAT GAT GCT GAG GGT GTA TGG AGT CCA GAC
 S   E   A   L   D   K   P   I   D   N   D   A   E   G   V   W   S   P   D 320        330        340        350        360        370
  *          *          *          *          *          *
ATT GAG CAG AGC TTC CAG GAA GCG CTA GCC ATC TAC CCA CCA TGT GGA CGG CGG AAG
 I   E   Q   S   F   Q   E   A   L   A   I   Y   P   P   C   G   R   R   K 380        390        400        410        420        430
          *          *          *          *          *          *
ATT ATC TTG TCA GAC GAA GGC AAG ATG TAT GGC CGA AAT GAG CTG ATT GCC CGT TAT
 I   I   L   S   D   E   G   K   M   Y   G   R   N   E   L   I   A   R   Y 440        450        460        470        480        490
          *          *          *          *          *          *
ATT AAG CTG AGA ACA GGG AAA ACA CGC ACA AGG AAA CAG GTA TCT AGT CAC ATC CAG
 I   K   L   R   T   G   K   T   R   T   R   K   Q   V   S   S   H   I   Q
```

FIG. 2(b)

```
         500         510         520         530         540
          *           *           *           *           *
GTC CTG GCA AGG CGG AAA GCC AGA GAG ATC CAA GCC AAG CTC AAG AAA ACT CAG GTA
 V   L   A   R   R   K   A   R   E   I   Q   A   K   L   K   K   T   Q   V
                                                             _____

550         560         570         580         590         600
     *           *           *           *           *           *
GAC AAA TAT GAC TTT TCC AGT GAA AAG GAC CAG ACA GCT AAA GAT AAA GCT ATG CAG
 D   K   Y   D   F   S   S   E   K   D   Q   T   A   K   D   K   A   M   Q
_____

610         620         630         640         650         660
     *           *           *           *           *           *
AGT ATC GCT ACA ATG TCA TCT GCC CAG ATA ATC TCT GCA ACT GCC TTC CAT AGT AAA
 S   I   A   T   M   S   S   A   Q   I   I   S   A   T   A   F   H   S   K 670         680         690         700         710
          *           *           *           *           *
ATG GCC TTG CCA GGT CTC CCA CGA TCA GCC TAT CCT GCT GTT TCT GGG TTT TGG CAA
 M   A   L   P   G   L   P   R   S   A   Y   P   A   V   S   G   F   W   Q 720         730         740         750         760         770
 *           *           *           *           *           *
GGA GCT TTG CCA GGC CAA GCT GGA TCT TCA CAA GAT GTG AAA CCT TTT ACT CAA CAA
 G   A   L   P   G   Q   A   G   S   S   Q   D   V   K   P   F   T   Q   Q 780         790         800         810         820         830
     *           *           *           *           *           *
CCC TAT GCT CTA CAG CCT TCA CTG CCA TTA CCA GGG TTT GAC TCT CCC ACT GGC CTC
 P   Y   A   L   Q   P   S   L   P   L   P   G   F   D   S   P   T   G   L 840         850         860         870         880
          *           *           *           *           *
CCA CCT TCA TCA TCA ACA CCA GCT TGG CAA GGA CGA AGG GTT GCT AGC TCC AAA CTT
 P   P   S   S   S   T   P   A   W   Q   G   R   R   V   A   S   S   K   L
```

FIG. 2(c)

```
      890         900         910         920         930         940
       *           *           *           *           *           *
TGG ATG TTA GAA TTC TCT GCA TTC TTG GAA CAA CAG CAA GAT CAA GAC ACG TAT AAC
 W   M   L   E   F   S   A   F   L   E   Q   Q   Q   D   Q   D   T   Y   N 950         960         970         980         990        1000
       *           *           *           *           *           *
AAA CAC CTG TTT GTG CAC ATC GGG CAG TCA AAT CCC AGC TAC AGT GAT CCC TAC CTT
 K   H   L   F   V   H   I   G   Q   S   N   P   S   Y   S   D   P   Y   L 1010        1020        1030        1040        1050        1060
       *           *           *           *           *           *
GAG GCA GTG GAT ATC CGA CAA ATC TAT GAC AAG TTC CCT GAG AAA AAA GGG GGC CTG
 E   A   V   D   I   R   Q   I   Y   D   K   F   P   E   K   K   G   G   L 1070        1080        1090        1100        1110
       *           *           *           *           *
AAG GAG CTG TTT GAA AGG GGG CCA GCA AAT GCC TTC TTC CTC GTC AAA TTC TGG GCT
 K   E   L   F   E   R   G   P   A   N   A   F   F   L   V   K   F   W   A 1120        1130        1140        1150        1160        1170
  *           *           *           *           *           *
GAT TTG AAC ACC AAT ATT GAA GAT GAA TCC AGA TCT TTC TAT GGT GTT TCC AGT CAA
 D   L   N   T   N   I   E   D   E   S   R   S   F   Y   G   V   S   S   Q 1180        1190        1200        1210        1220        1230
       *           *           *           *           *           *
TAT GAG AGC CCA GAA AAT ATG GTC ATT ACC TGT TCC ACT AAA GTG TGT TCC TTT GGA
 Y   E   S   P   E   N   M   V   I   T   C   S   T   K   V   C   S   F   G 1240        1250        1260        1270        1280
       *           *           *           *           *
AAG CAG GTG GTG GAG AAA GTG GAG ACA GAG TAT GCA CAC TAT GAA AAT GGA CAC TAT
 K   Q   V   V   E   K   V   E   T   E   Y   A   H   Y   E   N   G   H   Y
```

FIG. 2(d)

```
     1290        1300        1310        1320        1330        1340
       *           *           *           *           *           *
  GCC TAT CGC ATT CAT CGT TCT CCT CTC TGT GAA TAC ATG ATA AAC TTC ATT CAT AAA
   A   Y   R   I   H   R   S   P   L   C   E   Y   M   I   N   F   I   H   K 1350        1360        1370        1380        1390        1400
       *           *           *           *           *           *
  CTC AAG CAC CTT CCT GAG AAG TAC ATG ATG AAC AGT GTA CTG GAG AAC TTT ACT ATC
   L   K   H   L   P   E   K   Y   M   M   N   S   V   L   E   N   F   T   I 1410        1420        1430        1440        1450
       *           *           *           *           *
  TTA CAG GTT GTG ACA AAC AGG GAC ACA CAG GAG ACC TTG CTG TGC ATA GCA TAT GTT
   L   Q   V   V   T   N   R   D   T   Q   E   T   L   L   C   I   A   Y   V 1460        1470        1480        1490        1500        1510
  *           *           *           *           *           *
  TTT GAG GTG TCA GCT AGT GAC CAT GGT GCC CAG CAT CAC ATC TAC CGG CTG GTG AAG
   F   E   V   S   A   S   D   H   G   A   Q   H   H   I   Y   R   L   V   K 1520        1530        1540        1550        1560        1570
       *           *           *           *           *           *
  GAC TAG AGA CTA TCT GCC CTG AGT CAT CCA TGA GAT GCG TGT CTG AGG AAA AAG TCT
   D   *   R   L   S   A   L   S   H   P   *   D   A   C   L   R   K   K   S 1580        1590        1600        1610        1620        1630
       *           *           *           *           *           *
  GTG CTT GAA AAT CCC TTG ACT CTT TTC ACC AAA TTG AAA AAT AAA CCG CAG ATA CTG
   V   L   E   N   P   L   T   L   F   T   K   L   K   N   K   P   Q   I   L 1640        1650        1660
       *           *           *
  TGT ATT TTC AGA AAA GTA AAA AAA AAA AAA AAA AAA
   C   I   F   R   K   V   K   K   K   K   K
```

FIG. 3

TEA DOMAIN

```
TEF-1A    1 LELLAGTIT-SEWSSPASPEGSNDSGGEALDKPIDMQAEGVWSPDIEQSFQEALAIYPPCGRRKIILSDEGKMYGRNELIARYIKLRTGKTRTRKQVSSHIQVLARRKAREIQA
bTEF-1    1 .EP.S..GSE..AENME-RM.DSA......................................................................... S.DFHS

TEF-1A  115 KLK*DQTAKDKAMQSIATMSSAQLISATAFHSKMALPGLPRSAYPAVSGFWQ-GAL-PGQAGSSQDVKPFTQQPYALQPSL--PLP*GFDSPTGLPPSSSTPAWQGRRV
bTEF-1  108 .......G.HM.A...........V....I.N.LG...I..PTP.GAP....-P.MIQT.P........V..A.PI.AVIA.I...E-.ASA.A..V........SI

TEF-1A  218 ASSKLWMLEPSAFLEQQQDQDTYNKHELFVHIGQSMPSYSDPYLEAVDTRQIYDKFPEKKGGLKELFERGPANAPPLVKFWADINTNIEDESRSFVGVSSQYESPENMVI
bTEF-1  212 GIT..RLV...........R.P.S..........HA.H....L.S..............GK..Q..............C..Q.DAGA...T......S...TV

TEF-1A  327 TCSTKVCSFGKQVVEKVETEYAHYENGHYAYRIHRSPLCEYMINFIHKLKHLPEKYMMNSVLENFTILQVTNRDTQETLLCIAYVFEVSASDHGAQHHIYRLVKD
bTEF-1  321 .............RF..RFV..N..M...............................L........................M.C......N.E..........
```

```
TCCACCGCGGNGGCGGNCGCTGCTCTCGGCTGTCGATGGATCCCCCGGCTGCAGGAATTCCGGCTGCTCCGTCCGTCGTGCAG      360
CCCGGCTGNCACCGCTGCTCTCGGGTTGAGTTCTGTGAGTTGCATTCCCGGCCCCGCTGAGCTTGGTTCCCTACGGGACTCCGGAGCTTGCA
GCACTCTCGCATTCCTACCGCCCTCCCCCGGNCCATCCCGGCACCGGCTCCGGTTCGTCCGGYCCACTCCCGGCTCCCGTG
GMCGGYCCAGCCCTCCGGAGCACGGCAGGTTGTCTCTGTCCGTGGGGCTCGGCTCAGAGCCAGCAGCACCATAGCGTC      3
                                                                  I  A  S
CAACAGCTGGAAGCGCCAGCAGCAGCCCGGGGAAGATGGCCAGGGAAGATGGCCTGGACAATGACGCCGAGG      450
N  S  W  N  A  S  S  P  G  E  R  E  D  G  Q  D  G  M  D  K  S  L  D  N  D  A  E  G      33
AGTGTGGAGCCCGGACATTGAGCAGGAGCTTCCAGGAGGCTTACCCCCCTGCCGGGAAGATCATCCTCTCGGATGA      540
V  W  S  P  D  I  E  Q  S  F  Q  E  A  L  A  I  Y  P  P  C  G  R  R  K  I  I  L  S  D  E      63
AGGCAAGATGTACGGTCGTAACGAACTGGCGCTACATCAAGCTGCGGACAGGGAAGACACGGAAGAAGCAGGTCTCTAGCCA      630
G  K  M  Y  G  R  N  E  L  A  R  Y  I  K  L  R  T  G  K  T  R  T  K  Q  V  S  S  H      93
CTTGCAGGTTCTTGCCCGACGGGAGAAATCTCGGGAGATTCGTCCAAGCTGAAGGCCATGAACTTGGACCAAGTCTCCAAAGACAAGGCTTT      720
L  Q  V  L  A  R  R  E  I  S  G  D  S  S  K  L  K  A  M  N  L  D  Q  V  S  K  D  K  A  F      123
CCAGAGCATGGCGTCCATGTCTCTTCTGCTCAGATTGTGTCGGCAGCGTCCAGCAGCTCACAGAACAGCTCAGCCCCCTCCTCCTTCCTCAGGC      810
Q  S  M  A  S  M  S  S  A  Q  I  V  S  A  S  V  L  Q  N  K  L  S  P  P  P  P  L  P  Q  A      153
CGTCTTTTCTGCTGCCCCCAGGTTTTGGAGTGGGCCGATCCGAGACCCTCTCAGGACATTAAACCATTTGCACAACCAGC      900
V  F  S  A  A  P  R  F  W  S  G  P  I  P  G  Q  P  G  P  S  Q  D  I  K  P  F  A  Q  P  A      183
TTACCCCATCCAGCCACCATGCCTCCATCACTAGCCAGTTATGAGCCCTTGGCCCCACTGCCTCAGCCGTGCCGGTCTG      990
Y  P  I  Q  P  P  M  P  P  S  L  A  S  Y  E  P  L  A  P  L  P  P  A  A  S  A  V  P  V  W      213
GCAGGACCGCACCATCGCCTCTGCACGGGCAGACGAATCCCTCGTACAGTGACCCTCTGCCTTCATGGAGGTGCCGGGGATGCCGAAACGTATAGCAA     1080
Q  D  R  T  I  A  S  A  K  L  R  L  L  E  Y  S  A  F  M  E  V  P  R  D  A  E  T  Y  S  K      243
ACACCTCTTCGTGCACATCGGGCAGACTAACCCTCGTGTACAGTGACCCTCTGCTGGAGGGCTATGGACATCCGCCAGATCTATGACAAGTT     1170
H  L  F  V  H  I  G  Q  T  N  P  S  Y  S  D  P  L  E  A  M  D  I  R  Q  I  Y  D  K  F      273
CCCTGAGAAGAAGGGTGGCCTCAAGGAGCTCTATGAGCGTGGGCCCCAGAACTCCTTCTTCCTCAAGTTTTGGGCGGATCTGAACAG     1260
P  E  K  K  G  G  L  K  E  L  Y  E  R  G  P  Q  N  S  F  F  L  K  F  W  A  D  L  N  S      303
```

*FIG. 5B*

```
CACAATCCAGGATGGGCCAGGACTTTCTATGGTGTCAGCAGTCAATACAGCAGCCAGAGAACATGACCATCACAGTGTCCACCAAGGT  1350
  T  I  Q  D  G  P  G  T  F  Y  G  V  S  S  Q  Y  S  S  A  E  N  M  T  I  T  V  S  T  K  V     333
GTGCTCCTTTGGGAAGCAGGTTGTGGAGAAGGTGGAGACAGAGTATGCACGGTTGGAGAACAGCCGCTTTGTTCTACCGCATTCACCGCTC  1440
  C  S  F  G  K  Q  V  V  E  K  V  E  T  E  Y  A  R  L  E  N  S  R  F  V  Y  R  I  H  R  S     363
CCCCATGTGCGAATACATGATTAACTTCATCCACAAACTGAAGCATCTCCCGGAGAAGTACATGATGAACAGCGTCCTGGAGAATTTCAC  1530
  P  M  C  E  Y  M  I  N  F  I  H  K  L  K  H  L  P  E  K  Y  M  M  N  S  V  L  E  N  F  T     393
CATCCTGCAGGTTGTTACCAACAGGGATACCCAGGAAACCCTGCTCTGCATCGCCTTCGTGTTTGAGGTGTCCACCAGCGAGCACGGTGC  1620
  I  L  Q  V  V  T  N  R  D  T  Q  E  T  L  L  C  I  A  F  V  F  E  V  S  T  S  E  H  G  A     423
CCAGCATCATGTCTACAAGTTGGTGAAGGACTAGGGGCTTCGGGACAGGAGTCATTGGAAGAGAGGAGGATGAGGAGGAAGAACAAGAAA  1710
  Q  H  H  V  Y  K  L  V  K  D  *                                                              433
GAAGTNCCGCCTGTTGTGCCTCCCCAGCCCCCGGCCCAGGAGTCATTGGAAGAGAGGAGGATGAGGAGGAAGAAGAACAAGAAA
AGCAATAACCAAAAAGACTGACTTGTGATCGCAGATGTTTTCTACTTTAGGAACAGTTTTTCAATAAATATGTATATTAAAAAAAAAA      1897
AAAAAAAA
```

*FIG. 5BB*

```
NTEF-1  30: PIDN DAEGVWSDPIEQSFQEALAIYPPCGRRKIILSDEGKMYGRNELIARYIKLRTGKTRTRKQVSSHIQVL ARRKSRDFHSKLK
RTEF1   37: ....  ........................................................................A.EIQA.....
SD      88: LSSA  ........................S...............................................L.EIQA.I...
DTEF-1A 30: SL..  ...................................K.............L..............................EISGDS.....
DTEF-1B 30: SL..  ................................................................................K.V.STGWHQ-
```

FIG. 5C

```
DTEF-1A           AAGAAGCAGGTCTCTAGCCACTTGCAGGTTCTTGCCCGACGGGAAATCTCGGGAGATTCGTCCAAGCTGAAG
           87 K   K  Q  V  S  S  H  L  Q  V  L  A  R  R  R  E  I  S  G  D  S  S  K  L  K 110

DTEF-1B          AGGAAGCAGGTGTCCAGCCACATCCAGGTTCTAGCTCGGGAAGAAGGTGCGGAGTACAGGTTGGCATCAA
           87 R  K  Q  V  S  S  H  I  Q  V  L  A  R  K  K  K  V  R  S  T  G  W  H  Q 109
```

FIG. 5D

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: misc_feature
        ( B ) LOCATION: 1..7
        ( D ) OTHER INFORMATION: /standard_name= "M-CAT canonical sequence"

( x i ) SEQUENCE DESCRIPTION: SEQ ID NO:1:

```
CATTCCT                                                                          7
```

( 2 ) INFORMATION FOR SEQ ID NO:2:

( i ) SEQUENCE CHARACTERISTICS:
        ( A ) LENGTH: 1627 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 185..1480
        ( D ) OTHER INFORMATION: /product="TEF-1A"

( x i ) SEQUENCE DESCRIPTION: SEQ ID NO:2:

```
TCATACCAAC  TCTCATTCCA  CGCGTTCCTC  GTTTACTCCT  TTAAAACTCC  AGGGAAAATA        60

AAAACCCTCT  CTTTTCTTCC  CAAATTCTGG  CGGAACTGGC  CTCCCCCCGC  CGCCGTGCAG       120

TCTCGCCGTC  CGGCCCGCCG  CTCCGTACTC  TTCAGGTTCT  GAGTCTGCTT  CTCCACGTGG       180

CACC TTG GAG CTT CTA GCT GGC ACC ATT ACC TCC GAG TGG AGC TCT CCT            229
     Leu Glu Leu Leu Ala Gly Thr Ile Thr Ser Glu Trp Ser Ser Pro
      1               5                  10                  15

GCC TCC CCT GAG GGG AGC AAC GAT TCA GGG GGC AGT GAG GCC TTG GAC             277
Ala Ser Pro Glu Gly Ser Asn Asp Ser Gly Gly Ser Glu Ala Leu Asp
                20                  25                  30

AAA CCA ATT GAC AAT GAT GCT GAG GGT GTA TGG AGT CCA GAC ATT GAG             325
Lys Pro Ile Asp Asn Asp Ala Glu Gly Val Trp Ser Pro Asp Ile Glu
                    35                  40                  45

CAG AGC TTC CAG GAA GCG CTA GCC ATC TAC CCA CCA TGT GGA CGG CGG             373
Gln Ser Phe Gln Glu Ala Leu Ala Ile Tyr Pro Pro Cys Gly Arg Arg
                50                  55                  60

AAG ATT ATC TTG TCA GAC GAA GGC AAG ATG TAT GGC CGA AAT GAG CTG             421
Lys Ile Ile Leu Ser Asp Glu Gly Lys Met Tyr Gly Arg Asn Glu Leu
 65                  70                  75

ATT GCC CGT TAT ATT AAG CTG AGA ACA GGG AAA ACA CGC ACA AGG AAA             469
```

-continued

| | | | | | | | | | | | | | | | | |
|---|---|---|---|---|---|---|---|---|---|---|---|---|---|---|---|---|
| Ile | Ala | Arg | Tyr | Ile | Lys | Leu | Arg | Thr | Gly | Lys | Thr | Arg | Thr | Arg | Lys | |
| 80 | | | | 85 | | | | | 90 | | | | | 95 | | |
| CAG | GTA | TCT | AGT | CAC | ATC | CAG | GTC | CTG | GCA | AGG | CGG | AAA | GCC | AGA | GAG | 517 |
| Gln | Val | Ser | Ser | His | Ile | Gln | Val | Leu | Ala | Arg | Arg | Lys | Ala | Arg | Glu | |
| | | | 100 | | | | | 105 | | | | | 110 | | | |
| ATC | CAA | GCC | AAG | CTC | AAG | GAC | CAG | ACA | GCT | AAA | GAT | AAA | GCT | ATG | CAG | 565 |
| Ile | Gln | Ala | Lys | Leu | Lys | Asp | Gln | Thr | Ala | Lys | Asp | Lys | Ala | Met | Gln | |
| | | | 115 | | | | 120 | | | | | 125 | | | | |
| AGT | ATC | GCT | ACA | ATG | TCA | TCT | GCC | CAG | ATA | ATC | TCT | GCA | ACT | GCC | TTC | 613 |
| Ser | Ile | Ala | Thr | Met | Ser | Ser | Ala | Gln | Ile | Ile | Ser | Ala | Thr | Ala | Phe | |
| | | 130 | | | | 135 | | | | | 140 | | | | | |
| CAT | AGT | AAA | ATG | GCC | TTG | CCA | GGT | CTC | CCA | CGA | TCA | GCC | TAT | CCT | GCT | 661 |
| His | Ser | Lys | Met | Ala | Leu | Pro | Gly | Leu | Pro | Arg | Ser | Ala | Tyr | Pro | Ala | |
| | 145 | | | | 150 | | | | | 155 | | | | | | |
| GTT | TCT | GGG | TTT | TGG | CAA | GGA | GCT | TTG | CCA | GGC | CAA | GCT | GGA | TCT | TCA | 709 |
| Val | Ser | Gly | Phe | Trp | Gln | Gly | Ala | Leu | Pro | Gly | Gln | Ala | Gly | Ser | Ser | |
| 160 | | | | | 165 | | | | | 170 | | | | | 175 | |
| CAA | GAT | GTG | AAA | CCT | TTT | ACT | CAA | CAA | CCC | TAT | GCT | CTA | CAG | CCT | TCA | 757 |
| Gln | Asp | Val | Lys | Pro | Phe | Thr | Gln | Gln | Pro | Tyr | Ala | Leu | Gln | Pro | Ser | |
| | | | | 180 | | | | | 185 | | | | | 190 | | |
| CTG | CCA | TTA | CCA | GGG | TTT | GAC | TCT | CCC | ACT | GGC | CTC | CCA | CCT | TCA | TCA | 805 |
| Leu | Pro | Leu | Pro | Gly | Phe | Asp | Ser | Pro | Thr | Gly | Leu | Pro | Pro | Ser | Ser | |
| | | | 195 | | | | | 200 | | | | | 205 | | | |
| TCA | ACA | CCA | GCT | TGG | CAA | GGA | CGA | AGG | GTT | GCT | AGC | TCC | AAA | CTT | TGG | 853 |
| Ser | Thr | Pro | Ala | Trp | Gln | Gly | Arg | Arg | Val | Ala | Ser | Ser | Lys | Leu | Trp | |
| | | 210 | | | | | 215 | | | | | 220 | | | | |
| ATG | TTA | GAA | TTC | TCT | GCA | TTC | TTG | GAA | CAA | CAG | CAA | GAT | CAA | GAC | ACG | 901 |
| Met | Leu | Glu | Phe | Ser | Ala | Phe | Leu | Glu | Gln | Gln | Gln | Asp | Gln | Asp | Thr | |
| | 225 | | | | | 230 | | | | | 235 | | | | | |
| TAT | AAC | AAA | CAC | CTG | TTT | GTG | CAC | ATC | GGG | CAG | TCA | AAT | CCC | AGC | TAC | 949 |
| Tyr | Asn | Lys | His | Leu | Phe | Val | His | Ile | Gly | Gln | Ser | Asn | Pro | Ser | Tyr | |
| 240 | | | | | 245 | | | | | 250 | | | | | 255 | |
| AGT | GAT | CCC | TAC | CTT | GAG | GCA | GTG | GAT | ATC | CGA | CAA | ATC | TAT | GAC | AAG | 997 |
| Ser | Asp | Pro | Tyr | Leu | Glu | Ala | Val | Asp | Ile | Arg | Gln | Ile | Tyr | Asp | Lys | |
| | | | | 260 | | | | | 265 | | | | | 270 | | |
| TTC | CCT | GAG | AAA | AAA | GGG | GGC | CTG | AAG | GAG | CTG | TTT | GAA | AGG | GGG | CCA | 1045 |
| Phe | Pro | Glu | Lys | Lys | Gly | Gly | Leu | Lys | Glu | Leu | Phe | Glu | Arg | Gly | Pro | |
| | | | 275 | | | | | 280 | | | | | 285 | | | |
| GCA | AAT | GCC | TTC | TTC | CTC | GTC | AAA | TTC | TGG | GCT | GAT | TTG | AAC | ACC | AAT | 1093 |
| Ala | Asn | Ala | Phe | Phe | Leu | Val | Lys | Phe | Trp | Ala | Asp | Leu | Asn | Thr | Asn | |
| | | 290 | | | | | 295 | | | | | 300 | | | | |
| ATT | GAA | GAT | GAA | TCC | AGA | TCT | TTC | TAT | GGT | GTT | TCC | AGT | CAA | TAT | GAG | 1141 |
| Ile | Glu | Asp | Glu | Ser | Arg | Ser | Phe | Tyr | Gly | Val | Ser | Ser | Gln | Tyr | Glu | |
| | 305 | | | | | 310 | | | | | 315 | | | | | |
| AGC | CCA | GAA | AAT | ATG | GTC | ATT | ACC | TGT | TCC | ACT | AAA | GTG | TGT | TCC | TTT | 1189 |
| Ser | Pro | Glu | Asn | Met | Val | Ile | Thr | Cys | Ser | Thr | Lys | Val | Cys | Ser | Phe | |
| 320 | | | | | 325 | | | | | 330 | | | | | 335 | |
| GGA | AAG | CAG | GTG | GTG | GAG | AAA | GTG | GAG | ACA | GAG | TAT | GCA | CAC | TAT | GAA | 1237 |
| Gly | Lys | Gln | Val | Val | Glu | Lys | Val | Glu | Thr | Glu | Tyr | Ala | His | Tyr | Glu | |
| | | | | 340 | | | | | 345 | | | | | 350 | | |
| AAT | GGA | CAC | TAT | GCC | TAT | CGC | ATT | CAT | CGT | TCT | CCT | CTC | TGT | GAA | TAC | 1285 |
| Asn | Gly | His | Tyr | Ala | Tyr | Arg | Ile | His | Arg | Ser | Pro | Leu | Cys | Glu | Tyr | |
| | | | 355 | | | | | 360 | | | | | 365 | | | |
| ATG | ATA | AAC | TTC | ATT | CAT | AAA | CTC | AAG | CAC | CTT | CCT | GAG | AAG | TAC | ATG | 1333 |
| Met | Ile | Asn | Phe | Ile | His | Lys | Leu | Lys | His | Leu | Pro | Glu | Lys | Tyr | Met | |
| | | 370 | | | | | 375 | | | | | 380 | | | | |
| ATG | AAC | AGT | GTA | CTG | GAG | AAC | TTT | ACT | ATC | TTA | CAG | GTT | GTG | ACA | AAC | 1381 |
| Met | Asn | Ser | Val | Leu | Glu | Asn | Phe | Thr | Ile | Leu | Gln | Val | Val | Thr | Asn | |
| | 385 | | | | | 390 | | | | | 395 | | | | | |
| AGG | GAC | ACA | CAG | GAG | ACC | TTG | CTG | TGC | ATA | GCA | TAT | GTT | TTT | GAG | GTG | 1429 |

|     |     |     |     |     |     |     |     |     |     |     |     |     |     |     |     |
|-----|-----|-----|-----|-----|-----|-----|-----|-----|-----|-----|-----|-----|-----|-----|-----|
| Arg | Asp | Thr | Gln | Glu | Thr | Leu | Leu | Cys | Ile | Ala | Tyr | Val | Phe | Glu | Val |
| 400 |     |     |     |     | 405 |     |     |     | 410 |     |     |     |     | 415 |     |

| TCA | GCT | AGT | GAC | CAT | GGT | GCC | CAG | CAT | CAC | ATC | TAC | CGG | CTG | GTG | AAG | 1477 |
|-----|-----|-----|-----|-----|-----|-----|-----|-----|-----|-----|-----|-----|-----|-----|-----|------|
| Ser | Ala | Ser | Asp | His | Gly | Ala | Gln | His | His | Ile | Tyr | Arg | Leu | Val | Lys |      |
|     |     |     |     | 420 |     |     |     | 425 |     |     |     |     |     | 430 |     |      |

GAC TAGAGACTAT CTGCCCTGAG TCATCCATGA GATGCGTGTC TGAGGAAAAA 1530
Asp

GTCTGTGCTT GAAAATCCCT TGACTCTTTT CACCAAATTG AAAAATAAAC CGCAGATACT 1590

GTGTATTTTC AGAAAAGTAA AAAAAAAAAA AAAAAAA 1627

( 2 ) INFORMATION FOR SEQ ID NO:3:

( i ) SEQUENCE CHARACTERISTICS:
        ( A ) LENGTH: 432 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| Leu | Glu | Leu | Leu | Ala | Gly | Thr | Ile | Thr | Ser | Glu | Trp | Ser | Ser | Pro | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Pro | Glu | Gly | Ser | Asn | Asp | Ser | Gly | Ser | Glu | Ala | Leu | Asp | Lys |
|-----|-----|-----|-----|-----|-----|-----|-----|-----|-----|-----|-----|-----|-----|-----|
|     |     |     | 20  |     |     |     |     | 25  |     |     |     | 30  |     |     |

| Pro | Ile | Asp | Asn | Asp | Ala | Glu | Gly | Val | Trp | Ser | Pro | Asp | Ile | Glu | Gln |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ser | Phe | Gln | Glu | Ala | Leu | Ala | Ile | Tyr | Pro | Pro | Cys | Gly | Arg | Arg | Lys |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ile | Ile | Leu | Ser | Asp | Glu | Gly | Lys | Met | Tyr | Gly | Arg | Asn | Glu | Leu | Ile |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ala | Arg | Tyr | Ile | Lys | Leu | Arg | Thr | Gly | Lys | Thr | Arg | Thr | Arg | Lys | Gln |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Val | Ser | Ser | His | Ile | Gln | Val | Leu | Ala | Arg | Arg | Lys | Ala | Arg | Glu | Ile |
|-----|-----|-----|-----|-----|-----|-----|-----|-----|-----|-----|-----|-----|-----|-----|-----|
|     |     |     | 100 |     |     |     |     | 105 |     |     |     | 110 |     |     |     |

| Gln | Ala | Lys | Leu | Lys | Asp | Gln | Thr | Ala | Lys | Asp | Lys | Ala | Met | Gln | Ser |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Ile | Ala | Thr | Met | Ser | Ser | Ala | Gln | Ile | Ile | Ser | Ala | Thr | Ala | Phe | His |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Ser | Lys | Met | Ala | Leu | Pro | Gly | Leu | Pro | Arg | Ser | Ala | Tyr | Pro | Ala | Val |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Ser | Gly | Phe | Trp | Gln | Gly | Ala | Leu | Pro | Gly | Gln | Ala | Gly | Ser | Ser | Gln |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Asp | Val | Lys | Pro | Phe | Thr | Gln | Gln | Pro | Tyr | Ala | Leu | Gln | Pro | Ser | Leu |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Pro | Leu | Pro | Gly | Phe | Asp | Ser | Pro | Thr | Gly | Leu | Pro | Pro | Ser | Ser | Ser |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Thr | Pro | Ala | Trp | Gln | Gly | Arg | Arg | Val | Ala | Ser | Ser | Lys | Leu | Trp | Met |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Leu | Glu | Phe | Ser | Ala | Phe | Leu | Glu | Gln | Gln | Gln | Asp | Gln | Asp | Thr | Tyr |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Asn | Lys | His | Leu | Phe | Val | His | Ile | Gly | Gln | Ser | Asn | Pro | Ser | Tyr | Ser |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Asp | Pro | Tyr | Leu | Glu | Ala | Val | Asp | Ile | Arg | Gln | Ile | Tyr | Asp | Lys | Phe |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Pro | Glu | Lys | Lys | Gly | Gly | Leu | Lys | Glu | Leu | Phe | Glu | Arg | Gly | Pro | Ala |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| | | | | | | | | | | | | | | |
|---|---|---|---|---|---|---|---|---|---|---|---|---|---|---|
| Asn | Ala | Phe | Phe | Leu | Val | Lys | Phe | Trp | Ala | Asp | Leu | Asn | Thr | Asn | Ile |
| | 290 | | | | 295 | | | | | 300 | | | | |
| Glu | Asp | Glu | Ser | Arg | Ser | Phe | Tyr | Gly | Val | Ser | Ser | Gln | Tyr | Glu | Ser |
| 305 | | | | | 310 | | | | | 315 | | | | | 320 |
| Pro | Glu | Asn | Met | Val | Ile | Thr | Cys | Ser | Thr | Lys | Val | Cys | Ser | Phe | Gly |
| | | | | 325 | | | | | 330 | | | | | 335 | |
| Lys | Gln | Val | Val | Glu | Lys | Val | Glu | Thr | Glu | Tyr | Ala | His | Tyr | Glu | Asn |
| | | | 340 | | | | | 345 | | | | | 350 | | |
| Gly | His | Tyr | Ala | Tyr | Arg | Ile | His | Arg | Ser | Pro | Leu | Cys | Glu | Tyr | Met |
| | | 355 | | | | | 360 | | | | | 365 | | | |
| Ile | Asn | Phe | Ile | His | Lys | Leu | Lys | His | Leu | Pro | Glu | Lys | Tyr | Met | Met |
| | 370 | | | | | 375 | | | | | 380 | | | | |
| Asn | Ser | Val | Leu | Glu | Asn | Phe | Thr | Ile | Leu | Gln | Val | Val | Thr | Asn | Arg |
| 385 | | | | | 390 | | | | | 395 | | | | | 400 |
| Asp | Thr | Gln | Glu | Thr | Leu | Leu | Cys | Ile | Ala | Tyr | Val | Phe | Glu | Val | Ser |
| | | | | 405 | | | | | 410 | | | | | 415 | |
| Ala | Ser | Asp | His | Gly | Ala | Gln | His | His | Ile | Tyr | Arg | Leu | Val | Lys | Asp |
| | | | 420 | | | | | 425 | | | | | 430 | | |

( 2 ) INFORMATION FOR SEQ ID NO:4:

( i ) SEQUENCE CHARACTERISTICS:
        ( A ) LENGTH: 1666 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 185..1519
        ( D ) OTHER INFORMATION: /product="TEF-1B"

( i x ) FEATURE:
        ( A ) NAME/KEY: misc_feature
        ( B ) LOCATION: 536..571
        ( D ) OTHER INFORMATION: /product="KTQVDKYDFSSEK"

( x i ) SEQUENCE DESCRIPTION: SEQ ID NO:4:

```
TCATACCAAC TCTCATTCCA CGCGTTCCTC GTTTACTCCT TTAAAACTCC AGGGAAAATA        60

AAAACCCTCT CTTTTCTTCC CAAATTCTGG CGGAACTGGC CTCCCCCCGC CGCCGTGCAG       120

TCTCGCCGTC CGGCCCGCCG CTCCGTACTC TTCAGGTTCT GAGTCTGCTT CTCCACGTGG       180
```

| | | | | | | | | | | | | | | | |
|---|---|---|---|---|---|---|---|---|---|---|---|---|---|---|---|
| CACC | TTG | GAG | CTT | CTA | GCT | GGC | ACC | ATT | ACC | TCC | GAG | TGG | AGC | TCT | CCT | 229 |
| | Leu | Glu | Leu | Leu | Ala | Gly | Thr | Ile | Thr | Ser | Glu | Trp | Ser | Ser | Pro | |
| | 1 | | | | 5 | | | | | 10 | | | | | 15 | |
| GCC | TCC | CCT | GAG | GGG | AGC | AAC | GAT | TCA | GGG | GGC | AGT | GAG | GCC | TTG | GAC | 277 |
| Ala | Ser | Pro | Glu | Gly | Ser | Asn | Asp | Ser | Gly | Gly | Ser | Glu | Ala | Leu | Asp | |
| | | | | 20 | | | | | 25 | | | | | 30 | | |
| AAA | CCA | ATT | GAC | AAT | GAT | GCT | GAG | GGT | GTA | TGG | AGT | CCA | GAC | ATT | GAG | 325 |
| Lys | Pro | Ile | Asp | Asn | Asp | Ala | Glu | Gly | Val | Trp | Ser | Pro | Asp | Ile | Glu | |
| | | | 35 | | | | | 40 | | | | | 45 | | | |
| CAG | AGC | TTC | CAG | GAA | GCG | CTA | GCC | ATC | TAC | CCA | CCA | TGT | GGA | CGG | CGG | 373 |
| Gln | Ser | Phe | Gln | Glu | Ala | Leu | Ala | Ile | Tyr | Pro | Pro | Cys | Gly | Arg | Arg | |
| | | 50 | | | | | 55 | | | | | 60 | | | | |
| AAG | ATT | ATC | TTG | TCA | GAC | GAA | GGC | AAG | ATG | TAT | GGC | CGA | AAT | GAG | CTG | 421 |
| Lys | Ile | Ile | Leu | Ser | Asp | Glu | Gly | Lys | Met | Tyr | Gly | Arg | Asn | Glu | Leu | |
| | 65 | | | | | 70 | | | | | 75 | | | | | |
| ATT | GCC | CGT | TAT | ATT | AAG | CTG | AGA | ACA | GGG | AAA | ACA | CGC | ACA | AGG | AAA | 469 |
| Ile | Ala | Arg | Tyr | Ile | Lys | Leu | Arg | Thr | Gly | Lys | Thr | Arg | Thr | Arg | Lys | |
| | 80 | | | | | 85 | | | | | 90 | | | | | 95 |

| | | | | | | | | | | | | | | | | |
|---|---|---|---|---|---|---|---|---|---|---|---|---|---|---|---|---|
| CAG | GTA | TCT | AGT | CAC | ATC | CAG | GTC | CTG | GCA | AGG | CGG | AAA | GCC | AGA | GAG | 517 |
| Gln | Val | Ser | Ser | His 100 | Ile | Gln | Val | Leu 105 | Ala | Arg | Arg | Lys | Ala 110 | Arg | Glu | |
| ATC | CAA | GCC | AAG | CTC | AAG | AAA | ACT | CAG | GTA | GAC | AAA | TAT | GAC | TTT | TCC | 565 |
| Ile | Gln | Ala | Lys 115 | Leu | Lys | Lys | Thr | Gln 120 | Val | Asp | Lys | Tyr | Asp 125 | Phe | Ser | |
| AGT | GAA | AAG | GAC | CAG | ACA | GCT | AAA | GAT | AAA | GCT | ATG | CAG | AGT | ATC | GCT | 613 |
| Ser | Glu | Lys | Asp 130 | Gln | Thr | Ala | Lys 135 | Asp | Lys | Ala | Met | Gln 140 | Ser | Ile | Ala | |
| ACA | ATG | TCA | TCT | GCC | CAG | ATA | ATC | TCT | GCA | ACT | GCC | TTC | CAT | AGT | AAA | 661 |
| Thr | Met 145 | Ser | Ser | Ala | Gln | Ile 150 | Ile | Ser | Ala | Thr | Ala 155 | Phe | His | Ser | Lys | |
| ATG | GCC | TTG | CCA | GGT | CTC | CCA | CGA | TCA | GCC | TAT | CCT | GCT | GTT | TCT | GGG | 709 |
| Met 160 | Ala | Leu | Pro | Gly | Leu 165 | Pro | Arg | Ser | Ala | Tyr 170 | Pro | Ala | Val | Ser | Gly 175 | |
| TTT | TGG | CAA | GGA | GCT | TTG | CCA | GGC | CAA | GCT | GGA | TCT | TCA | CAA | GAT | GTG | 757 |
| Phe | Trp | Gln | Gly | Ala 180 | Leu | Pro | Gly | Gln | Ala 185 | Gly | Ser | Ser | Gln | Asp 190 | Val | |
| AAA | CCT | TTT | ACT | CAA | CAA | CCC | TAT | GCT | CTA | CAG | CCT | TCA | CTG | CCA | TTA | 805 |
| Lys | Pro | Phe | Thr 195 | Gln | Gln | Pro | Tyr | Ala 200 | Leu | Gln | Pro | Ser | Leu 205 | Pro | Leu | |
| CCA | GGG | TTT | GAC | TCT | CCC | ACT | GGC | CTC | CCA | CCT | TCA | TCA | TCA | ACA | CCA | 853 |
| Pro | Gly | Phe 210 | Asp | Ser | Pro | Thr | Gly 215 | Leu | Pro | Pro | Ser | Ser 220 | Ser | Thr | Pro | |
| GCT | TGG | CAA | GGA | CGA | AGG | GTT | GCT | AGC | TCC | AAA | CTT | TGG | ATG | TTA | GAA | 901 |
| Ala | Trp | Gln 225 | Gly | Arg | Arg | Val | Ala 230 | Ser | Ser | Lys | Leu | Trp 235 | Met | Leu | Glu | |
| TTC | TCT | GCA | TTC | TTG | GAA | CAA | CAG | CAA | GAT | CAA | GAC | ACG | TAT | AAC | AAA | 949 |
| Phe | Ser | Ala | Phe 240 | Leu | Glu | Gln | Gln | Gln 245 | Asp | Gln | Asp | Thr | Tyr 250 | Asn | Lys 255 | |
| CAC | CTG | TTT | GTG | CAC | ATC | GGG | CAG | TCA | AAT | CCC | AGC | TAC | AGT | GAT | CCC | 997 |
| His | Leu | Phe | Val | His 260 | Ile | Gly | Gln | Ser | Asn 265 | Pro | Ser | Tyr | Ser | Asp 270 | Pro | |
| TAC | CTT | GAG | GCA | GTG | GAT | ATC | CGA | CAA | ATC | TAT | GAC | AAG | TTC | CCT | GAG | 1045 |
| Tyr | Leu | Glu | Ala | Val 275 | Asp | Ile | Arg | Gln | Ile 280 | Tyr | Asp | Lys | Phe | Pro 285 | Glu | |
| AAA | AAA | GGG | GGC | CTG | AAG | GAG | CTG | TTT | GAA | AGG | GGG | CCA | GCA | AAT | GCC | 1093 |
| Lys | Lys | Gly | Gly 290 | Leu | Lys | Glu | Leu | Phe 295 | Glu | Arg | Gly | Pro | Ala 300 | Asn | Ala | |
| TTC | TTC | CTC | GTC | AAA | TTC | TGG | GCT | GAT | TTG | AAC | ACC | AAT | ATT | GAA | GAT | 1141 |
| Phe | Phe | Leu 305 | Val | Lys | Phe | Trp | Ala 310 | Asp | Leu | Asn | Thr | Asn 315 | Ile | Glu | Asp | |
| GAA | TCC | AGA | TCT | TTC | TAT | GGT | GTT | TCC | AGT | CAA | TAT | GAG | AGC | CCA | GAA | 1189 |
| Glu | Ser | Arg | Ser 320 | Phe | Tyr | Gly | Val | Ser 325 | Ser | Gln | Tyr | Glu | Ser 330 | Pro | Glu 335 | |
| AAT | ATG | GTC | ATT | ACC | TGT | TCC | ACT | AAA | GTG | TGT | TCC | TTT | GGA | AAG | CAG | 1237 |
| Asn | Met | Val | Ile | Thr 340 | Cys | Ser | Thr | Lys | Val 345 | Cys | Ser | Phe | Gly | Lys 350 | Gln | |
| GTG | GTG | GAG | AAA | GTG | GAG | ACA | GAG | TAT | GCA | CAC | TAT | GAA | AAT | GGA | CAC | 1285 |
| Val | Val | Glu | Lys 355 | Val | Glu | Thr | Glu | Tyr 360 | Ala | His | Tyr | Glu | Asn 365 | Gly | His | |
| TAT | GCC | TAT | CGC | ATT | CAT | CGT | TCT | CCT | CTC | TGT | GAA | TAC | ATG | ATA | AAC | 1333 |
| Tyr | Ala | Tyr 370 | Arg | Ile | His | Arg | Ser 375 | Pro | Leu | Cys | Glu | Tyr 380 | Met | Ile | Asn | |
| TTC | ATT | CAT | AAA | CTC | AAG | CAC | CTT | CCT | GAG | AAG | TAC | ATG | ATG | AAC | AGT | 1381 |
| Phe | Ile | His 385 | Lys | Leu | Lys | His | Leu 390 | Pro | Glu | Lys | Tyr | Met 395 | Met | Asn | Ser | |
| GTA | CTG | GAG | AAC | TTT | ACT | ATC | TTA | CAG | GTT | GTG | ACA | AAC | AGG | GAC | ACA | 1429 |
| Val | Leu | Glu | Asn 400 | Phe | Thr | Ile | Leu | Gln 405 | Val | Val | Thr | Asn | Arg 410 | Asp | Thr 415 | |

```
CAG GAG ACC TTG CTG TGC ATA GCA TAT GTT TTT GAG GTG TCA GCT AGT          1477
Gln Glu Thr Leu Leu Cys Ile Ala Tyr Val Phe Glu Val Ser Ala Ser
            420                 425                 430

GAC CAT GGT GCC CAG CAT CAC ATC TAC CGG CTG GTG AAG GAC                  1519
Asp His Gly Ala Gln His His Ile Tyr Arg Leu Val Lys Asp
            435                 440                 445

TAGAGACTAT CTGCCCTGAG TCATCCATGA GATGCGTGTC TGAGGAAAAA GTCTGTGCTT        1579

GAAAATCCCT TGACTCTTTT CACCAAATTG AAAAATAAAC CGCAGATACT GTGTATTTC         1639

AGAAAAGTAA AAAAAAAAAA AAAAAA                                             1666
```

( 2 ) INFORMATION FOR SEQ ID NO:5:

( i ) SEQUENCE CHARACTERISTICS:
        ( A ) LENGTH: 445 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Leu Glu Leu Leu Ala Gly Thr Ile Thr Ser Glu Trp Ser Ser Pro Ala
 1               5                   10                  15

Ser Pro Glu Gly Ser Asn Asp Ser Gly Gly Ser Glu Ala Leu Asp Lys
                20                  25                  30

Pro Ile Asp Asn Asp Ala Glu Gly Val Trp Ser Pro Asp Ile Glu Gln
            35                  40                  45

Ser Phe Gln Glu Ala Leu Ala Ile Tyr Pro Pro Cys Gly Arg Arg Lys
        50                  55                  60

Ile Ile Leu Ser Asp Glu Gly Lys Met Tyr Gly Arg Asn Glu Leu Ile
65                  70                  75                  80

Ala Arg Tyr Ile Lys Leu Arg Thr Gly Lys Thr Arg Thr Arg Lys Gln
                85                  90                  95

Val Ser Ser His Ile Gln Val Leu Ala Arg Arg Lys Ala Arg Glu Ile
                100                 105                 110

Gln Ala Lys Leu Lys Lys Thr Gln Val Asp Lys Tyr Asp Phe Ser Ser
            115                 120                 125

Glu Lys Asp Gln Thr Ala Lys Asp Lys Ala Met Gln Ser Ile Ala Thr
        130                 135                 140

Met Ser Ser Ala Gln Ile Ile Ser Ala Thr Ala Phe His Ser Lys Met
145                 150                 155                 160

Ala Leu Pro Gly Leu Pro Arg Ser Ala Tyr Pro Ala Val Ser Gly Phe
                165                 170                 175

Trp Gln Gly Ala Leu Pro Gly Gln Ala Gly Ser Ser Gln Asp Val Lys
            180                 185                 190

Pro Phe Thr Gln Gln Pro Tyr Ala Leu Gln Pro Ser Leu Pro Leu Pro
        195                 200                 205

Gly Phe Asp Ser Pro Thr Gly Leu Pro Pro Ser Ser Thr Pro Ala
        210                 215                 220

Trp Gln Gly Arg Arg Val Ala Ser Ser Lys Leu Trp Met Leu Glu Phe
225                 230                 235                 240

Ser Ala Phe Leu Glu Gln Gln Gln Asp Gln Asp Thr Tyr Asn Lys His
                245                 250                 255

Leu Phe Val His Ile Gly Gln Ser Asn Pro Ser Tyr Ser Asp Pro Tyr
            260                 265                 270

Leu Glu Ala Val Asp Ile Arg Gln Ile Tyr Asp Lys Phe Pro Glu Lys
        275                 280                 285
```

-continued

| Lys | Gly | Gly | Leu | Lys | Glu | Leu | Phe | Glu | Arg | Gly | Pro | Ala | Asn | Ala | Phe |
| | 290 | | | | 295 | | | | | 300 | | | | | |

| Phe | Leu | Val | Lys | Phe | Trp | Ala | Asp | Leu | Asn | Thr | Asn | Ile | Glu | Asp | Glu |
| 305 | | | | | 310 | | | | | 315 | | | | | 320 |

| Ser | Arg | Ser | Phe | Tyr | Gly | Val | Ser | Ser | Gln | Tyr | Glu | Ser | Pro | Glu | Asn |
| | | | | 325 | | | | | 330 | | | | | 335 | |

| Met | Val | Ile | Thr | Cys | Ser | Thr | Lys | Val | Cys | Ser | Phe | Gly | Lys | Gln | Val |
| | | | 340 | | | | 345 | | | | | 350 | | | |

| Val | Glu | Lys | Val | Glu | Thr | Glu | Tyr | Ala | His | Tyr | Glu | Asn | Gly | His | Tyr |
| | | 355 | | | | 360 | | | | | 365 | | | | |

| Ala | Tyr | Arg | Ile | His | Arg | Ser | Pro | Leu | Cys | Glu | Tyr | Met | Ile | Asn | Phe |
| 370 | | | | | 375 | | | | | 380 | | | | | |

| Ile | His | Lys | Leu | Lys | His | Leu | Pro | Glu | Lys | Tyr | Met | Met | Asn | Ser | Val |
| 385 | | | | | 390 | | | | | 395 | | | | | 400 |

| Leu | Glu | Asn | Phe | Thr | Ile | Leu | Gln | Val | Val | Thr | Asn | Arg | Asp | Thr | Gln |
| | | | | 405 | | | | | 410 | | | | | 415 | |

| Glu | Thr | Leu | Leu | Cys | Ile | Ala | Tyr | Val | Phe | Glu | Val | Ser | Ala | Ser | Asp |
| | | | 420 | | | | | 425 | | | | | 430 | | |

| His | Gly | Ala | Gln | His | His | Ile | Tyr | Arg | Leu | Val | Lys | Asp |
| | | 435 | | | | | 440 | | | | | 445 |

(2) INFORMATION FOR SEQ ID NO:6:

(i) SEQUENCE CHARACTERISTICS:
        (A) LENGTH: 426 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (A) ORGANISM: Homo sapiens (ix) FEATURE:
        (A) NAME/KEY: Protein
        (B) LOCATION: 1..426
        (D) OTHER INFORMATION: /note= "Human TEF-1"

(xi) SEQUENCE DESCRIPTION: SEQ ID NO:6:

| Ile | Glu | Pro | Ser | Ser | Trp | Ser | Gly | Ser | Glu | Ser | Pro | Ala | Glu | Asn | Met |
| 1 | | | | 5 | | | | | 10 | | | | | 15 | |

| Glu | Arg | Met | Ser | Asp | Ser | Ala | Asp | Lys | Pro | Ile | Asp | Asn | Asp | Ala | Glu |
| | | | 20 | | | | | 25 | | | | | 30 | | |

| Gly | Val | Trp | Ser | Pro | Asp | Ile | Glu | Gln | Ser | Phe | Gln | Glu | Ala | Leu | Ala |
| | | | 35 | | | | | 40 | | | | | 45 | | |

| Ile | Tyr | Pro | Pro | Cys | Gly | Arg | Arg | Lys | Ile | Ile | Leu | Ser | Asp | Glu | Gly |
| | | 50 | | | | | 55 | | | | | 60 | | | |

| Lys | Met | Tyr | Gly | Arg | Asn | Glu | Leu | Ile | Ala | Arg | Tyr | Ile | Lys | Leu | Arg |
| 65 | | | | | 70 | | | | | 75 | | | | | 80 |

| Thr | Gly | Lys | Thr | Arg | Thr | Arg | Lys | Gln | Val | Ser | Ser | His | Ile | Gln | Val |
| | | | | 85 | | | | | 90 | | | | | 95 | |

| Leu | Ala | Arg | Arg | Lys | Gly | Arg | Asp | Phe | His | Ser | Lys | Leu | Lys | Asp | Gln |
| | | | 100 | | | | | 105 | | | | | 110 | | |

| Thr | Ala | Lys | Asp | Lys | Ala | Leu | Gln | His | Met | Ala | Ala | Met | Ser | Ser | Ala |
| | | | 115 | | | | | 120 | | | | | 125 | | |

| Gln | Ile | Val | Ser | Ala | Thr | Ala | Ile | His | Asn | Lys | Leu | Gly | Leu | Pro | Gly |
| | | 130 | | | | | 135 | | | | | 140 | | | |

| Ile | Pro | Arg | Pro | Thr | Pro | Pro | Gly | Ala | Pro | Gly | Phe | Trp | Pro | Gly | Met |
| 145 | | | | | 150 | | | | | 155 | | | | | 160 |

```
Ile Gln Thr Gly Gln Pro Gly Ser Ser Gln Asp Val Lys Pro Phe Val
            165             170             175

Gln Gln Ala Tyr Pro Ile Gln Pro Ala Val Thr Ala Pro Ile Pro Gly
            180             185             190

Phe Glu Pro Ala Ser Ala Pro Ala Ser Ser Val Pro Ala Trp Gln Gly
            195             200             205

Arg Ser Ile Gly Thr Thr Lys Leu Arg Leu Val Glu Phe Ser Ala Phe
    210             215             220

Leu Glu Gln Gln Arg Asp Pro Asp Ser Tyr Asn Lys His Leu Phe Val
225             230             235                         240

His Ile Gly His Ala Asn His Ser Tyr Ser Asp Pro Leu Leu Glu Ser
                245             250                         255

Val Asp Ile Arg Gln Ile Tyr Asp Lys Phe Pro Glu Lys Lys Gly Gly
            260             265             270

Leu Lys Glu Leu Phe Gly Lys Gly Pro Gln Asn Ala Phe Phe Leu Val
        275             280             285

Lys Phe Trp Ala Asp Leu Asn Cys Asn Ile Gln Asp Asp Ala Gly Ala
290                     295             300

Phe Tyr Gly Val Thr Ser Gln Tyr Glu Ser Ser Glu Asn Met Thr Val
305             310             315                         320

Thr Cys Ser Thr Lys Val Cys Ser Phe Gly Lys Gln Val Val Glu Lys
            325             330             335

Val Glu Thr Glu Tyr Ala Arg Phe Glu Asn Gly Arg Phe Val Tyr Arg
            340             345             350

Ile Asn Arg Ser Pro Met Cys Glu Tyr Met Ile Asn Phe Ile His Lys
        355             360             365

Leu Lys His Leu Pro Glu Lys Tyr Met Met Asn Ser Val Leu Glu Asn
    370             375             380

Phe Thr Ile Leu Leu Val Val Thr Asn Arg Asp Thr Gln Glu Thr Leu
385             390             395                         400

Leu Cys Met Ala Cys Val Phe Glu Val Ser Asn Ser Glu His Gly Ala
                405             410                         415

Gln His His Ile Tyr Arg Leu Val Lys Asp
            420             425
```

( 2 ) INFORMATION FOR SEQ ID NO:7:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( i x ) FEATURE:
        ( A ) NAME/KEY: Peptide
        ( B ) LOCATION: 1..13
        ( D ) OTHER INFORMATION: /note= "The additional amino acids
            present in TEF-1B."

( x i ) SEQUENCE DESCRIPTION: SEQ ID NO:7:

```
Lys Thr Gln Val Asp Lys Tyr Asp Phe Ser Ser Glu Lys
1               5                   10
```

( 2 ) INFORMATION FOR SEQ ID NO:8:

( i ) SEQUENCE CHARACTERISTICS:
        ( A ) LENGTH: 7 base pairs
        ( B ) TYPE: nucleic acid (C) STRANDEDNESS: single
        (D) TOPOLOGY: linear (ii) MOLECULE TYPE: DNA (xi) SEQUENCE DESCRIPTION: SEQ ID NO:8:

C A T T C C A                                                                                7

(2) INFORMATION FOR SEQ ID NO:9:

(i) SEQUENCE CHARACTERISTICS:
        (A) LENGTH: 7 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..7
        (D) OTHER INFORMATION: /standard_name= "Sph-I binding site in SV40"

(xi) SEQUENCE DESCRIPTION: SEQ ID NO:9:

C A T G C T T                                                                                7

(2) INFORMATION FOR SEQ ID NO:10:

(i) SEQUENCE CHARACTERISTICS:
        (A) LENGTH: 7 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..7
        (D) OTHER INFORMATION: /standard_name= "Sph-II binding site in SV40"

(xi) SEQUENCE DESCRIPTION: SEQ ID NO:10:

C A T A C T T                                                                                7

(2) INFORMATION FOR SEQ ID NO:11:

(i) SEQUENCE CHARACTERISTICS:
        (A) LENGTH: 7 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..7
        (D) OTHER INFORMATION: /standard_name= "Cardiac Troponin C M-CAT binding element"

(xi) SEQUENCE DESCRIPTION: SEQ ID NO:11:

C A T T C C C                                                                                7

(2) INFORMATION FOR SEQ ID NO:12:

(i) SEQUENCE CHARACTERISTICS:
        (A) LENGTH: 7 base pairs
        (B) TYPE: nucleic acid
        (C) STRANDEDNESS: single
        (D) TOPOLOGY: linear ( i i ) MOLECULE TYPE: DNA ( i x ) FEATURE:
    ( A ) NAME/KEY: misc_feature
    ( B ) LOCATION: 1..7
    ( D ) OTHER INFORMATION: /standard_name= "Rat beta-Myosin
        Heavy Chain M-CAT binding element"

( x i ) SEQUENCE DESCRIPTION: SEQ ID NO:12:

CATACCA 7

( 2 ) INFORMATION FOR SEQ ID NO:13:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:13:

TCGGGTGTTG GGTACCTCTC TGC 23

( 2 ) INFORMATION FOR SEQ ID NO:14:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:14:

CCGAGCAGAG AGGTACCCAA CAC 23

( 2 ) INFORMATION FOR SEQ ID NO:15:

( i ) SEQUENCE CHARACTERISTICS:
    ( A ) LENGTH: 426 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:15:

```
Ile Glu Pro Ser Ser Trp Ser Gly Ser Glu Ser Pro Ala Glu Asn Met
 1               5                  10                  15
Glu Arg Met Ser Asp Ser Ala Asp Lys Pro Ile Asp Asn Asp Ala Glu
            20                  25                  30
Gly Val Trp Ser Pro Asp Ile Glu Gln Ser Phe Gln Glu Ala Leu Ala
        35                  40                  45
Ile Tyr Pro Pro Cys Gly Arg Arg Lys Ile Ile Leu Ser Asp Glu Gly
    50                  55                  60
Lys Met Tyr Gly Arg Asn Glu Leu Ile Ala Arg Tyr Ile Lys Leu Arg
65                  70                  75                  80
Thr Gly Lys Thr Arg Thr Arg Lys Gln Val Ser Ser His Ile Gln Val
                85                  90                  95
Leu Ala Arg Arg Lys Ser Arg Asp Phe His Ser Lys Leu Lys Asp Gln
            100                 105                 110
Thr Ala Lys Asp Lys Ala Leu Gln His Met Ala Ala Met Ser Ser Ala
        115                 120                 125
```

```
Gln Ile Val Ser Ala Thr Ala Ile His Asn Lys Leu Gly Leu Pro Gly
    130                 135                 140

Ile Pro Arg Pro Thr Phe Pro Gly Ala Pro Gly Phe Trp Pro Gly Met
145                 150                 155                 160

Ile Gln Thr Gly Gln Pro Gly Ser Ser Gln Asp Val Lys Pro Phe Val
                165                 170                 175

Gln Gln Ala Tyr Pro Ile Gln Pro Ala Val Thr Ala Pro Ile Pro Gly
            180                 185                 190

Phe Glu Pro Ala Ser Ala Pro Ala Pro Ser Val Pro Ala Trp Gln Gly
        195                 200                 205

Arg Ser Ile Gly Thr Thr Lys Leu Arg Leu Val Glu Phe Ser Ala Phe
    210                 215                 220

Leu Glu Gln Gln Arg Asp Pro Asp Ser Tyr Asn Lys His Leu Phe Val
225                 230                 235                 240

His Ile Gly His Ala Asn His Ser Tyr Ser Asp Pro Leu Leu Glu Ser
                245                 250                 255

Val Asp Ile Arg Gln Ile Tyr Asp Lys Phe Pro Glu Lys Lys Gly Gly
            260                 265                 270

Leu Lys Glu Leu Phe Gly Lys Gly Pro Gln Asn Ala Phe Phe Leu Val
        275                 280                 285

Lys Phe Trp Ala Asp Leu Asn Cys Asn Ile Gln Asp Asp Ala Gly Ala
290                 295                 300

Phe Tyr Gly Val Thr Ser Gln Tyr Glu Ser Ser Glu Asn Met Thr Val
305                 310                 315                 320

Thr Cys Ser Thr Lys Val Cys Ser Phe Gly Lys Gln Val Val Glu Lys
                325                 330                 335

Val Glu Thr Glu Tyr Ala Arg Phe Glu Asn Gly Arg Phe Val Tyr Arg
            340                 345                 350

Ile Asn Arg Ser Pro Met Cys Glu Tyr Met Ile Asn Phe Ile His Lys
        355                 360                 365

Leu Lys His Leu Pro Glu Lys Tyr Met Met Asn Ser Val Leu Glu Asn
370                 375                 380

Phe Thr Ile Leu Leu Val Val Thr Asn Arg Asp Thr Gln Glu Thr Leu
385                 390                 395                 400

Leu Cys Met Ala Cys Val Phe Glu Val Ser Asn Ser Glu His Gly Ala
                405                 410                 415

Gln His His Ile Tyr Arg Leu Val Lys Asp
            420                 425
```

( 2 ) INFORMATION FOR SEQ ID NO:16:

( i ) SEQUENCE CHARACTERISTICS:
        ( A ) LENGTH: 418 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:16:

```
Ile Glu Pro Ser Ser Trp Ser Gly Ser Glu Ser Pro Ala Glu Asp Ile
1               5                   10                  15

Glu Arg Met Ser Asp Ser Ala Asp Lys Pro Ile Asp Asn Asp Ala Glu
            20                  25                  30

Gly Val Trp Ser Pro Asp Ile Glu Gln Ser Phe Gln Glu Ala Leu Ala
        35                  40                  45

Ile Tyr Pro Pro Cys Gly Arg Arg Lys Ile Ile Leu Ser Asp Glu Gly
```

|       |       |       | 50    |       |       | 55    |       |       |       | 60    |       |       |       |       |
|-------|-------|-------|-------|-------|-------|-------|-------|-------|-------|-------|-------|-------|-------|-------|
| Lys 65 | Met | Tyr | Gly | Arg | Asn 70 | Glu | Leu | Ile | Ala | Arg 75 | Tyr | Ile | Lys | Leu | Arg 80 |

Lys Met Tyr Gly Arg Asn Glu Leu Ile Ala Arg Tyr Ile Lys Leu Arg
65                70                    75                       80

Thr Gly Lys Thr Arg Thr Arg Lys Gln Val Ser Ser His Ile Gln Val
            85                    90                       95

Leu Ala Arg Arg Lys Ser Arg Asp Phe His Ser Lys Leu Lys Val Thr
              100               105              110

Ser Met Asp Gln Thr Ala Lys Asp Lys Ala Leu Gln His Met Ala Ala
            115               120              125

Met Ser Ser Ala Gln Ile Val Ser Ala Thr Ala Ile His Asn Lys Leu
        130               135              140

Gly Leu Pro Gly Ile Pro Arg Pro Thr Phe Pro Gly Ala Pro Gly Phe
145                   150              155                   160

Trp Pro Gly Met Ile Gln Thr Gly Gln Pro Gly Ser Ser Gln Asp Val
                165               170                  175

Lys Pro Phe Val Gln Gln Ala Tyr Pro Ile Gln Pro Ser Val Thr Ala
            180               185              190

Pro Ile Ser Gly Phe Glu Pro Thr Ser Ala Pro Ala Pro Ser Val Pro
        195               200              205

Ala Trp Gln Gly Arg Ser Ile Gly Thr Thr Lys Leu Arg Leu Val Glu
    210               215              220

Phe Ser Ala Phe Leu Glu Gln Gln Arg Asp Pro Glu Ser Tyr Asn Lys
225               230              235                   240

His Leu Phe Val His Ile Gly His Ala Asn His Ser Tyr Ser Asp Pro
                245              250                  255

Leu Leu Glu Ser Val Asp Ile Arg Gln Ile Ile Asp Lys Phe Pro Glu
            260               265              270

Lys Glu Gly Gly Leu Lys Glu Leu Phe Gly Lys Gly Pro Gln Asn Ala
        275               280              285

Phe Phe Leu Val Lys Phe Trp Ala Asp Leu Asn Cys Asn Ile Gln Asp
290                   295              300

Asp Thr Gly Ala Phe Tyr Gly Val Thr Ser Gln Tyr Glu Ser Ser Glu
305               310              315                  320

Asn Met Thr Ile Thr Cys Ser Thr Lys Val Cys Ser Phe Gly Lys Gln
            325               330              335

Val Val Glu Lys Val Glu Xaa Glu Tyr Ala Arg Phe Glu Asn Xaa Arg
        340               345              350

Phe Val Tyr Arg Ile Asn Arg Ser Pro Met Cys Glu Tyr Met Ile Asn
        355               360              365

Phe Ile His Lys Leu Lys His Leu Pro Glu Lys Tyr Met Met Asn Ser
370                   375              380

Val Leu Glu Asn Phe Thr Ile Leu Leu Val Val Thr Asn Arg Asp Thr
385               390              395                   400

Gln Glu Thr Leu Leu Cys Met Ala Cys Val Phe Glu Val Ser Asn Ser
            405               410              415

Glu Gln ( 2 ) INFORMATION FOR SEQ ID NO:17:

( i ) SEQUENCE CHARACTERISTICS:
        ( A ) LENGTH: 425 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

| Ile | Thr | Ser | Glu | Trp | Ser | Ser | Pro | Ala | Ser | Pro | Glu | Gly | Ser | Asn | Asp |
| 1 | | | | 5 | | | | | 10 | | | | | 15 | |

| Ser | Gly | Gly | Ser | Glu | Ala | Leu | Asp | Lys | Pro | Ile | Asp | Asn | Asp | Ala | Glu |
| | | | 20 | | | | 25 | | | | | 30 | | | |

| Gly | Val | Trp | Ser | Pro | Asp | Ile | Glu | Gln | Ser | Phe | Gln | Glu | Ala | Leu | Ala |
| | | 35 | | | | | 40 | | | | | 45 | | | |

| Ile | Tyr | Pro | Pro | Cys | Gly | Arg | Arg | Lys | Ile | Ile | Leu | Ser | Asp | Glu | Gly |
| | 50 | | | | | 55 | | | | | 60 | | | | |

| Lys | Met | Tyr | Gly | Arg | Asn | Glu | Leu | Ile | Ala | Arg | Tyr | Ile | Lys | Leu | Arg |
| 65 | | | | | 70 | | | | | 75 | | | | | 80 |

| Thr | Gly | Lys | Thr | Arg | Thr | Arg | Lys | Gln | Val | Ser | Ser | His | Ile | Gln | Val |
| | | | | 85 | | | | | 90 | | | | | 95 | |

| Leu | Ala | Arg | Arg | Lys | Ala | Arg | Glu | Ile | Gln | Ala | Lys | Leu | Lys | Asp | Gln |
| | | | 100 | | | | 105 | | | | | 110 | | | |

| Thr | Ala | Lys | Asp | Lys | Ala | Met | Gln | Ser | Ile | Ala | Thr | Met | Ser | Ser | Ala |
| | | 115 | | | | | 120 | | | | | 125 | | | |

| Gln | Ile | Ile | Ser | Ala | Thr | Ala | Phe | His | Ser | Lys | Met | Ala | Leu | Pro | Gly |
| | 130 | | | | | 135 | | | | | 140 | | | | |

| Leu | Pro | Arg | Ser | Ala | Tyr | Pro | Ala | Val | Ser | Gly | Phe | Trp | Gln | Gly | Ala |
| 145 | | | | | 150 | | | | | 155 | | | | | 160 |

| Leu | Pro | Gly | Gln | Ala | Gly | Ser | Ser | Gln | Asp | Val | Lys | Pro | Phe | Thr | Gln |
| | | | | 165 | | | | | 170 | | | | | 175 | |

| Gln | Pro | Tyr | Ala | Leu | Gln | Pro | Ser | Leu | Pro | Leu | Pro | Gly | Phe | Asp | Ser |
| | | | 180 | | | | 185 | | | | | 190 | | | |

| Pro | Thr | Gly | Leu | Pro | Pro | Ser | Ser | Thr | Pro | Ala | Trp | Gln | Gly | Arg |
| | | 195 | | | | | 200 | | | | | 205 | | | |

| Arg | Val | Ala | Ser | Ser | Lys | Leu | Trp | Met | Leu | Glu | Phe | Ser | Ala | Phe | Leu |
| | 210 | | | | | 215 | | | | | 220 | | | | |

| Glu | Gln | Gln | Gln | Asp | Gln | Asp | Thr | Tyr | Asn | Lys | His | Leu | Phe | Val | His |
| 225 | | | | | 230 | | | | | 235 | | | | | 240 |

| Ile | Gly | Gln | Ser | Asn | Pro | Ser | Tyr | Ser | Asp | Pro | Tyr | Leu | Glu | Ala | Val |
| | | | | 245 | | | | | 250 | | | | | 255 | |

| Asp | Ile | Arg | Gln | Ile | Tyr | Asp | Lys | Phe | Pro | Glu | Lys | Lys | Gly | Gly | Leu |
| | | | 260 | | | | 265 | | | | | 270 | | | |

| Lys | Glu | Leu | Phe | Gly | Glu | Arg | Pro | Ala | Asn | Ala | Phe | Phe | Leu | Val | Lys |
| | | 275 | | | | | 280 | | | | | 285 | | | |

| Phe | Trp | Ala | Asp | Leu | Asn | Thr | Asn | Ile | Glu | Asp | Glu | Ser | Arg | Ser | Phe |
| | 290 | | | | | 295 | | | | | 300 | | | | |

| Tyr | Gly | Val | Ser | Ser | Gln | Tyr | Glu | Ser | Pro | Glu | Asn | Met | Val | Ile | Thr |
| 305 | | | | | 310 | | | | | 315 | | | | | 320 |

| Cys | Ser | Thr | Lys | Val | Cys | Ser | Phe | Gly | Lys | Gln | Val | Val | Glu | Lys | Val |
| | | | | 325 | | | | | 330 | | | | | 335 | |

| Glu | Thr | Glu | Tyr | Ala | His | Tyr | Glu | Asn | Gly | His | Tyr | Ala | Tyr | Arg | Ile |
| | | | 340 | | | | 345 | | | | | 350 | | | |

| His | Arg | Ser | Pro | Leu | Cys | Glu | Tyr | Met | Ile | Asn | Phe | Ile | His | Lys | Leu |
| | | 355 | | | | | 360 | | | | | 365 | | | |

| Lys | His | Leu | Pro | Glu | Lys | Tyr | Met | Met | Asn | Ser | Val | Leu | Glu | Asn | Phe |
| | 370 | | | | | 375 | | | | | 380 | | | | |

| Thr | Ile | Leu | Gln | Val | Val | Thr | Asn | Arg | Asp | Thr | Gln | Glu | Thr | Leu | Leu |
| 385 | | | | | 390 | | | | | 395 | | | | | 400 |

| Cys | Ile | Ala | Tyr | Val | Phe | Glu | Val | Ser | Ala | Ser | Asp | His | Gly | Ala | Gln |
| | | | | 405 | | | | | 410 | | | | | 415 | |

His His Ile Tyr Arg Leu Val Lys Asp
420                         425

( 2 ) INFORMATION FOR SEQ ID NO:18:

( i ) SEQUENCE CHARACTERISTICS:
       ( A ) LENGTH: 1897 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:18:

| | | | | | | |
|---|---|---|---|---|---|---|
| TCCACCGCGG | NGGCGGNCGC | TCTAGAACTA | GTGGATCCCC | CGGGCTGCAG | GAATTCCGCG | 60 |
| TCGCGTCCGT | CCGTCTGTCC | GTCCGTGCAG | CCCGGCTGNC | ACCCGCTGCT | CTCGGGTTGA | 120 |
| GTTCTGTGCA | TTTCCCGGCC | CCGCTGAGCT | TGGTTCCCTA | CGCGGACTCC | GGAGCTTGCA | 180 |
| GCACTCTCGC | ATTCCTACCG | CCCTCCCCCG | GNCCATCCCC | GGCACCGGCT | CCGGTCCCGG | 240 |
| TTCGGTCCCG | GYCCACTCCC | GGCTCCCGTG | GMCGGYCCAG | CCCTCCGGAG | CACGGAGCAG | 300 |
| GTTGTCTCGT | GTCCGTGGGG | GCTCGGGCTC | AGAGCCCAGA | GCAGCCAGCA | CCATAGCGTC | 360 |
| CAACAGCTGG | AACGCCAGCA | GCAGCCCCGG | GGAGGGGCGG | GAAGATGGCC | AGGACGGGAT | 420 |
| GGACAAGAGC | CTGGACAATG | ACGCCGAGGG | AGTGTGGAGC | CCGGACATTG | AGCAGAGCTT | 480 |
| CCAGGAGGCT | CTGGCAATCT | ACCCCCCCTG | CGGCCGGCGG | AAGATCATCC | TCTCGGATGA | 540 |
| AGGCAAGATG | TACGGTCGTA | ACGAACTGAT | TGCGCGCTAC | ATCAAGCTGC | GGACAGGGAA | 600 |
| GACACGGACA | AAGAAGCAGG | TCTCTAGCCA | CTTGCAGGTT | CTTGCCCGAC | GGGAAATCTC | 660 |
| GGGAGATTCG | TCCAAGCTGA | AGGCCATGAA | CTTGGACCAA | GTCTCCAAAG | ACAAGGCTTT | 720 |
| CCAGAGCATG | GCGTCCATGT | CTTCTGCTCA | GATTGTGTCG | GCCAGCGTCC | TACAGAACAA | 780 |
| GCTCAGCCCC | CCTCCTCCTC | TTCCTCAGGC | CGTCTTTTCT | GCTGCCCCA | GGTTTTGGAG | 840 |
| TGGGCCGATC | CCAGGACAGC | CTGGACCCTC | TCAGGACATT | AAACCATTTG | CACAACCAGC | 900 |
| TTACCCCATC | CAGCCACCCA | TGCCTCCATC | ACTAGCCAGT | TATGAGCCCT | TGGCCCCACT | 960 |
| GCCACCAGCT | GCCTCAGCCG | TGCCGGTCTG | GCAGGACCGC | ACCATCGCCT | CTGCCAAGCT | 1020 |
| GCGGCTCCTC | GAGTACTCTG | CCTTCATGGA | GGTGCCGCGG | GATGCCGAAA | CGTATAGCAA | 1080 |
| ACACCTCTTC | GTGCACATCG | GGCAGACGAA | TCCCTCGTAC | AGTGACCCTC | TGCTGGAGGC | 1140 |
| TATGGACATC | CGCCAGATCT | ATGACAAGTT | CCCTGAGAAG | AAGGGTGGCC | TCAAGGAGCT | 1200 |
| CTATGAGCGT | GGGCCCAGA | ACTCCTTCTT | CCTCCTCAAG | TTTTGGGCGG | ATCTGAACAG | 1260 |
| CACAATCCAG | GATGGGCCAG | GGACTTTCTA | TGGTGTCAGC | AGTCAATACA | GCAGCGCAGA | 1320 |
| GAACATGACC | ATCACAGTGT | CCACCAAGGT | GTGCTCCTTT | GGGAAGCAGG | TTGTGGAGAA | 1380 |
| GGTGGAGACA | GAGTATGCAC | GGTTGGAGAA | CAGCCGCTTT | GTCTACCGCA | TTCACCGCTC | 1440 |
| CCCCATGTGC | GAATACATGA | TTAACTTCAT | CCACAAACTG | AAGCATCTCC | GGAGAAGTA | 1500 |
| CATGATGAAC | AGCGTCCTGG | AGAATTTCAC | CATCCTGCAG | GTTGTTACCA | ACAGGGATAC | 1560 |
| CCAGGAAACC | CTGCTCTGCA | TCGCCTTCGT | GTTTGAGGTG | TCCACCAGCG | AGCACGGTGC | 1620 |
| CCAGCATCAT | GTCTACAAGT | TGGTGAAGGA | CTAGGGGCTT | CGGGACAGGA | GGGGGCTTGA | 1680 |
| GGGACACGGG | GATGTGGGGA | GGGTTGTTCA | GAAGTNCCGC | CTGTTGTGCC | TCCCCAGCCC | 1740 |
| CGCCAGGAGT | CATTGGAAGA | GAGGAGGATG | AGGAGGAGGA | GGAGAAGGAA | GAACAAGAAA | 1800 |
| AGCAATAACC | AAAAAAGACT | GACTTGTGAT | CGCAGATGTT | TTCTACTTTA | GGAACAGTTT | 1860 |
| TTCAATAAAT | ATGTATATTA | AAAAAAAAA | AAAAAA | | | 1897 |

( 2 ) INFORMATION FOR SEQ ID NO:19:

( i ) SEQUENCE CHARACTERISTICS:
        ( A ) LENGTH: 433 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:19:

```
Ile Ala Ser Asn Ser Trp Asn Ala Ser Ser Pro Gly Glu Gly Arg
 1               5                  10                  15

Glu Asp Gly Gln Asp Gly Met Asp Lys Ser Leu Asp Asn Asp Ala Glu
                20                  25                  30

Gly Val Trp Ser Pro Asp Ile Glu Gln Ser Phe Gln Glu Ala Leu Ala
            35                  40                  45

Ile Tyr Pro Pro Cys Gly Arg Arg Lys Ile Ile Leu Ser Asp Glu Gly
    50                  55                  60

Lys Met Tyr Gly Arg Asn Glu Leu Ile Ala Arg Tyr Ile Lys Leu Arg
65                  70                  75                  80

Thr Gly Lys Thr Arg Thr Lys Lys Gln Val Ser Ser His Leu Gln Val
                85                  90                  95

Leu Ala Arg Arg Glu Ile Ser Gly Asp Ser Ser Lys Leu Lys Ala Met
            100                 105                 110

Asn Leu Asp Gln Val Ser Lys Asp Lys Ala Phe Gln Ser Met Ala Ser
        115                 120                 125

Met Ser Ser Ala Gln Ile Val Ser Ala Ser Val Leu Gln Asn Lys Leu
130                 135                 140

Ser Pro Pro Pro Pro Leu Pro Gln Ala Val Phe Ser Ala Ala Pro Arg
145                 150                 155                 160

Phe Trp Ser Gly Pro Ile Pro Gly Gln Pro Gly Pro Ser Gln Asp Ile
                165                 170                 175

Lys Pro Phe Ala Gln Pro Ala Tyr Pro Ile Gln Pro Pro Met Pro Pro
            180                 185                 190

Ser Leu Ala Ser Tyr Glu Pro Leu Ala Pro Leu Pro Pro Ala Ala Ser
        195                 200                 205

Ala Val Pro Val Trp Gln Asp Arg Thr Ile Ala Ser Ala Lys Leu Arg
    210                 215                 220

Leu Leu Glu Tyr Ser Ala Phe Met Glu Val Pro Arg Asp Ala Glu Thr
225                 230                 235                 240

Tyr Ser Lys His Leu Phe Val His Ile Gly Gln Thr Asn Pro Ser Tyr
                245                 250                 255

Ser Asp Pro Leu Leu Glu Ala Met Asp Ile Arg Gln Ile Tyr Asp Lys
            260                 265                 270

Phe Pro Glu Lys Lys Gly Gly Leu Lys Glu Leu Tyr Glu Arg Gly Pro
        275                 280                 285

Gln Asn Ser Phe Phe Leu Leu Lys Phe Trp Ala Asp Leu Asn Ser Thr
    290                 295                 300

Ile Gln Asp Gly Pro Gly Thr Phe Tyr Gly Val Ser Ser Gln Tyr Ser
305                 310                 315                 320

Ser Ala Glu Asn Met Thr Ile Thr Val Ser Thr Lys Val Cys Ser Phe
                325                 330                 335

Gly Lys Gln Val Val Glu Lys Val Glu Thr Glu Tyr Ala Arg Leu Glu
            340                 345                 350
```

```
        Asn  Ser  Arg  Phe  Val  Tyr  Arg  Ile  His  Arg  Ser  Pro  Met  Cys  Glu  Tyr
                  355                      360                      365

Met  Ile  Asn  Phe  Ile  His  Lys  Leu  Lys  His  Leu  Pro  Glu  Lys  Tyr  Met
             370                      375                      380

Met  Asn  Ser  Val  Leu  Glu  Asn  Phe  Thr  Ile  Leu  Gln  Val  Val  Thr  Asn
        385                      390                      395                      400

Arg  Asp  Thr  Gln  Glu  Thr  Leu  Leu  Cys  Ile  Ala  Phe  Val  Phe  Glu  Val
                       405                      410                      415

Ser  Thr  Ser  Glu  His  Gly  Ala  Gln  His  His  Val  Tyr  Lys  Leu  Val  Lys
                       420                      425                      430

Asp
```

( 2 ) INFORMATION FOR SEQ ID NO:20:

( i ) SEQUENCE CHARACTERISTICS:
        ( A ) LENGTH: 1894 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

```
TCCACCGCGG  NGGCGGNCGC  TCTAGAACTA  GTGGATCCCC  CGGGCTGCAG  GAATTCCGCG    60

TCGCGTCCGT  CCGTCTGTCC  GTCCGTGCAG  CCCGGCTGNC  ACCCGCTGCT  CTCGGGTTGA   120

GTTCTGTGCA  TTTCCCGGCC  CCGCTGAGCT  TGGTTCCCTA  CGCGGACTCC  GGAGCTTGCA   180

GCACTCTCGC  ATTCCTACCG  CCCTCCCCCG  GNCCATCCCC  GGCACCGGCT  CCGGTCCCGG   240

TTCGGTCCCG  GYCCACTCCC  GGCTCCCGTG  GMCGGYCCAG  CCCTCCGGAG  CACGGAGCAG   300

GTTGTCTCGT  GTCCGTGGGG  GCTCGGGCTC  AGAGCCCAGA  GCAGCCAGCA  CCATAGCGTC   360

CAACAGCTGG  AACGCCAGCA  GCAGCCCCGG  GGAGGGGCGG  AAGATGGCC   AGGACGGGAT   420

GGACAAGAGC  CTGGACAATG  ACGCCGAGGG  AGTGTGGAGC  CCGGACATTG  AGCAGAGCTT   480

CCAGGAGGCT  CTGGCAATCT  ACCCCCCCTG  CGGCCGGCGG  AAGATCATCC  TCTCGGATGA   540

AGGCAAGATG  TACGGTCGTA  ACGAACTGAT  TGCGCGCTAC  ATCAAGCTGC  GGACAGGGAA   600

GACACGGACA  AGGAAGCAGG  TGTCCAGCCA  CATCCAGGTT  CTAGCTCGGA  AGAAGGTGCG   660

GAGTACAGGT  TGGCATCAAG  CCATGAACTT  GGACCAAGTC  TCCAAAGACA  AGGCTTTCCA   720

GAGCATGGCG  TCCATGTCTT  CTGCTCAGAT  TGTGTCGGCC  AGCGTCCTAC  AGAACAAGCT   780

CAGCCCCCCT  CCTCCTCTTC  CTCAGGCCGT  CTTTTCTGCT  GCCCCCAGGT  TTTGGAGTGG   840

GCCGATCCCA  GGACAGCCTG  GACCCTCTCA  GGACATTAAA  CCATTTGCAC  AACCAGCTTA   900

CCCCATCCAG  CCACCCATGC  CTCCATCACT  AGCCAGTTAT  GAGCCCTTGG  CCCCACTGCC   960

ACCAGCTGCC  TCAGCCGTGC  CGGTCTGGCA  GGACCGCACC  ATCGCCTCTG  CCAAGCTGCG  1020

GCTCCTCGAG  TACTCTGCCT  TCATGGAGGT  GCCGCGGGAT  GCCGAAACGT  ATAGCAAACA  1080

CCTCTTCGTG  CACATCGGGC  AGACGAATCC  CTCGTACAGT  GACCCTCTGC  TGGAGGCTAT  1140

GGACATCCGC  CAGATCTATG  ACAAGTTCCC  TGAGAAGAAG  GGTGGCCTCA  AGGAGCTCTA  1200

TGAGCGTGGG  CCCCAGAACT  CCTTCTTCCT  CCTCAAGTTT  GGGCGGATC   TGAACAGCAC  1260

AATCCAGGAT  GGGCCAGGGA  CTTTCTATGG  TGTCAGCAGT  CAATACAGCA  GCGCAGAGAA  1320

CATGACCATC  ACAGTGTCCA  CCAAGGTGTG  CTCCTTTGGG  AAGCAGGTTG  TGGAGAAGGT  1380

GGAGACAGAG  TATGCACGGT  TGGAGAACAG  CCGCTTTGTC  TACCGCATTC  ACCGCTCCCC  1440

CATGTGCGAA  TACATGATTA  ACTTCATCCA  CAAACTGAAG  CATCTCCCGG  AGAAGTACAT  1500
```

-continued

```
GATGAACAGC GTCCTGGAGA ATTTCACCAT CCTGCAGGTT GTTACCAACA GGGATACCCA    1560
GGAAACCCTG CTCTGCATCG CCTTCGTGTT TGAGGTGTCC ACCAGCGAGC ACGGTGCCCA    1620
GCATCATGTC TACAAGTTGG TGAAGGACTA GGGGCTTCGG GACAGGAGGG GGCTTGAGGG    1680
ACACGGGGAT GTGGGGAGGG TTGTTCAGAA GTNCCGCCTG TTGTGCCTCC CCAGCCCCGC    1740
CAGGAGTCAT TGGAAGAGAG GAGGATGAGG AGGAGGAGGA GAAGGAAGAA CAAGAAAAGC    1800
AATAACCAAA AAAGACTGAC TTGTGATCGC AGATGTTTTC TACTTTAGGA ACAGTTTTTC    1860
AATAAATATG TATATTAAAA AAAAAAAAAA AAAA                                1894
```

(2) INFORMATION FOR SEQ ID NO:21:

(i) SEQUENCE CHARACTERISTICS:
        (A) LENGTH: 432 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

```
Ile Ala Ser Asn Ser Trp Asn Ala Ser Ser Pro Gly Glu Gly Arg
 1               5                  10                  15

Glu Asp Gly Gln Asp Gly Met Asp Lys Ser Leu Asp Asn Asp Ala Glu
                20                  25                  30

Gly Val Trp Ser Pro Asp Ile Glu Gln Ser Phe Gln Glu Ala Leu Ala
            35                  40                  45

Ile Tyr Pro Pro Cys Gly Arg Arg Lys Ile Ile Leu Ser Asp Glu Gly
    50                  55                  60

Lys Met Tyr Gly Arg Asn Glu Leu Ile Ala Arg Tyr Ile Lys Leu Arg
65                  70                  75                  80

Thr Gly Lys Thr Arg Thr Arg Lys Gln Val Ser Ser His Ile Gln Val
                85                  90                  95

Leu Ala Arg Lys Lys Val Arg Ser Thr Gly Trp His Gln Ala Met Asn
            100                 105                 110

Leu Asp Gln Val Ser Lys Asp Lys Ala Phe Gln Ser Met Ala Ser Met
        115                 120                 125

Ser Ser Ala Gln Ile Val Ser Ala Ser Val Leu Gln Asn Lys Leu Ser
    130                 135                 140

Pro Pro Pro Pro Leu Pro Gln Ala Val Phe Ser Ala Ala Pro Arg Phe
145                 150                 155                 160

Trp Ser Gly Pro Ile Pro Gly Gln Pro Gly Pro Ser Gln Asp Ile Lys
                165                 170                 175

Pro Phe Ala Gln Pro Ala Tyr Pro Ile Gln Pro Pro Met Pro Pro Ser
            180                 185                 190

Leu Ala Ser Tyr Glu Pro Leu Ala Pro Leu Pro Pro Ala Ala Ser Ala
        195                 200                 205

Val Pro Val Trp Gln Asp Arg Thr Ile Ala Ser Ala Lys Leu Arg Leu
    210                 215                 220

Leu Glu Tyr Ser Ala Phe Met Glu Val Pro Arg Asp Ala Glu Thr Tyr
225                 230                 235                 240

Ser Lys His Leu Phe Val His Ile Gly Gln Thr Asn Pro Ser Tyr Ser
                245                 250                 255

Asp Pro Leu Leu Glu Ala Met Asp Ile Arg Gln Ile Tyr Asp Lys Phe
            260                 265                 270

Pro Glu Lys Lys Gly Gly Leu Lys Glu Leu Tyr Glu Arg Gly Pro Gln
        275                 280                 285
```

```
Asn  Ser  Phe  Phe  Leu  Leu  Lys  Phe  Trp  Ala  Asp  Leu  Asn  Ser  Thr  Ile
     290                 295                 300

Gln  Asp  Gly  Pro  Gly  Thr  Phe  Tyr  Gly  Val  Ser  Ser  Gln  Tyr  Ser  Ser
305                      310                 315                           320

Ala  Glu  Asn  Met  Thr  Ile  Thr  Val  Ser  Thr  Lys  Val  Cys  Ser  Phe  Gly
                    325                      330                      335

Lys  Gln  Val  Val  Glu  Lys  Val  Glu  Thr  Glu  Tyr  Ala  Arg  Leu  Glu  Asn
               340                      345                      350

Ser  Arg  Phe  Val  Tyr  Arg  Ile  His  Arg  Ser  Pro  Met  Cys  Glu  Tyr  Met
          355                      360                      365

Ile  Asn  Phe  Ile  His  Lys  Leu  Lys  His  Leu  Pro  Glu  Lys  Tyr  Met  Met
     370                      375                 380

Asn  Ser  Val  Leu  Glu  Asn  Phe  Thr  Ile  Leu  Gln  Val  Val  Thr  Asn  Arg
385                      390                      395                      400

Asp  Thr  Gln  Glu  Thr  Leu  Leu  Cys  Ile  Ala  Phe  Val  Phe  Glu  Val  Ser
                    405                 410                      415

Thr  Ser  Glu  His  Gly  Ala  Gln  His  His  Val  Tyr  Lys  Leu  Val  Lys  Asp
               420                 425                      430
```

(2) INFORMATION FOR SEQ ID NO:22:

(i) SEQUENCE CHARACTERISTICS:
        (A) LENGTH: 85 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Pro  Ile  Asp  Asn  Asp  Ala  Glu  Gly  Val  Trp  Ser  Pro  Asp  Ile  Glu  Gln
1                   5                        10                      15

Ser  Phe  Gln  Glu  Ala  Leu  Ala  Ile  Tyr  Pro  Pro  Cys  Gly  Arg  Arg  Lys
               20                  25                      30

Ile  Ile  Leu  Ser  Asp  Glu  Gly  Lys  Met  Tyr  Gly  Arg  Asn  Glu  Leu  Ile
          35                      40                      45

Ala  Arg  Tyr  Ile  Lys  Leu  Arg  Thr  Gly  Lys  Thr  Arg  Thr  Arg  Lys  Gln
     50                      55                      60

Val  Ser  Ser  His  Ile  Gln  Val  Leu  Ala  Arg  Arg  Lys  Ser  Arg  Asp  Phe
65                      70                      75                      80

His  Ser  Lys  Leu  Lys
               85
```

(2) INFORMATION FOR SEQ ID NO:23:

(i) SEQUENCE CHARACTERISTICS:
        (A) LENGTH: 85 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Pro  Ile  Asp  Asn  Asp  Ala  Glu  Gly  Val  Trp  Ser  Pro  Asp  Ile  Glu  Gln
1                   5                        10                      15

Ser  Phe  Gln  Glu  Ala  Leu  Ala  Ile  Tyr  Pro  Pro  Cys  Gly  Arg  Arg  Lys
               20                  25                      30

Ile  Ile  Leu  Ser  Asp  Glu  Gly  Lys  Met  Tyr  Gly  Arg  Asn  Glu  Leu  Ile
          35                      40                      45
```

```
             Ala Arg Tyr Ile Lys Leu Arg Thr Gly Lys Thr Arg Thr Arg Lys Gln
                  50                  55                  60

Val Ser Ser His Ile Gln Val Leu Ala Arg Arg Lys Ala Arg Glu Ile
             65                  70                  75                  80

Gln Ala Lys Leu Lys
                           85
```

( 2 ) INFORMATION FOR SEQ ID NO:24:

( i ) SEQUENCE CHARACTERISTICS:
        ( A ) LENGTH: 85 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

```
             Leu Ser Ser Ala Asp Ala Glu Gly Val Trp Ser Pro Asp Ile Glu Gln
             1               5                  10                  15

Ser Phe Gln Glu Ala Leu Ser Ile Tyr Pro Pro Cys Gly Arg Arg Lys
                           20                  25                  30

Ile Ile Leu Ser Asp Glu Gly Lys Met Tyr Gly Arg Asn Glu Leu Ile
                       35                  40                  45

Ala Arg Tyr Ile Lys Leu Arg Thr Gly Lys Thr Arg Thr Arg Lys Gln
                  50                  55                  60

Val Ser Ser His Ile Gln Val Leu Ala Arg Arg Lys Leu Arg Glu Ile
             65                  70                  75                  80

Gln Ala Lys Ile Lys
                           85
```

( 2 ) INFORMATION FOR SEQ ID NO:25:

( i ) SEQUENCE CHARACTERISTICS:
        ( A ) LENGTH: 85 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

```
             Ser Leu Asp Asn Asp Ala Glu Gly Val Trp Ser Pro Asp Ile Glu Gln
             1               5                  10                  15

Ser Phe Gln Glu Ala Leu Ala Ile Tyr Pro Pro Cys Gly Arg Arg Lys
                           20                  25                  30

Ile Ile Leu Ser Asp Glu Gly Lys Met Tyr Gly Arg Asn Glu Leu Ile
                       35                  40                  45

Ala Arg Tyr Ile Lys Leu Arg Thr Gly Lys Thr Arg Thr Lys Lys Gln
                  50                  55                  60

Val Ser Ser His Leu Gln Val Leu Ala Arg Arg Glu Ile Ser Gly Asp
             65                  70                  75                  80

Ser Ser Lys Leu Lys
                           85
```

( 2 ) INFORMATION FOR SEQ ID NO:26:

( i ) SEQUENCE CHARACTERISTICS:
        ( A ) LENGTH: 84 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

| Ser | Leu | Asp | Asn | Asp | Ala | Glu | Gly | Val | Trp | Ser | Pro | Asp | Ile | Glu | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Phe | Gln | Glu | Ala | Leu | Ala | Ile | Tyr | Pro | Pro | Cys | Gly | Arg | Arg | Lys |
|     |     |     | 20  |     |     |     |     | 25  |     |     |     |     | 30  |     |     |
| Ile | Ile | Leu | Ser | Asp | Glu | Gly | Lys | Met | Tyr | Gly | Arg | Asn | Glu | Leu | Ile |
|     |     |     | 35  |     |     |     | 40  |     |     |     |     | 45  |     |     |     |
| Ala | Arg | Tyr | Ile | Lys | Leu | Arg | Thr | Gly | Lys | Thr | Arg | Thr | Arg | Lys | Gln |
|     |     | 50  |     |     |     | 55  |     |     |     |     | 60  |     |     |     |     |
| Val | Ser | Ser | His | Ile | Gln | Val | Leu | Ala | Arg | Lys | Lys | Val | Arg | Ser | Thr |
| 65  |     |     |     |     | 70  |     |     |     |     | 75  |     |     |     |     | 80  |
| Gly | Trp | His | Gln |     |     |     |     |     |     |     |     |     |     |     |     |

( 2 ) INFORMATION FOR SEQ ID NO:27:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

```
AAGAAGCAGG TCTCTAGCCA CTTGCAGGTT CTTGCCCGAC GGGAAATCTC GGGAGATTCG      60
TCCAAGCTGA AG                                                          72
```

( 2 ) INFORMATION FOR SEQ ID NO:28:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

| Lys | Lys | Gln | Val | Ser | Ser | His | Leu | Gln | Val | Leu | Ala | Arg | Arg | Glu | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Gly | Asp | Ser | Ser | Lys | Leu | Lys |     |     |     |     |     |     |     |     |
|     |     |     |     | 20  |     |     |     |     |     |     |     |     |     |     |     |

( 2 ) INFORMATION FOR SEQ ID NO:29:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

```
AGGAAGCAGG TGTCCAGCCA CATCCAGGTT CTAGCTCGGA AGAAGGTGCG GAGTACAGGT      60
TGGCATCAA                                                              69
```

( 2 ) INFORMATION FOR SEQ ID NO:30:

( i ) SEQUENCE CHARACTERISTICS:
        ( A ) LENGTH: 23 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:30:

```
Arg Lys Gln Val Ser Ser His Ile Gln Val Leu Ala Arg Lys Lys Val
1               5                   10                  15
Arg Ser Thr Gly Trp His Gln
            20
```

(2) INFORMATION FOR SEQ ID NO:31:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (primer)

(xi) SEQUENCE DESCRIPTION: SEQ ID NO:31:

TGGAGYCCNG AYATYAGARC A                                   21

(2) INFORMATION FOR SEQ ID NO:32:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (primer)

(xi) SEQUENCE DESCRIPTION: SEQ ID NO:32:

ATCATRTAYT CRCACATBGG                                     20

DTEF-1 ISOFORMS AND USES THEREOF

This application is a continuation-in-part of PCT/US95/01526, filed on Feb. 6, 1995, which is a continuation-in-part of application Ser. No. 08/191,493, filed on Feb. 4, 1994, now abandoned the full disclosure of which is incorporated herein by reference.

This invention was made with Government support under Grant Nos. HL35561, GM32018, and HL43821 awarded by the National Institutes of Health. The Government has certain rights in this invention.

FIELD OF THE INVENTION

This invention relates to transcriptional regulation of genes, and more particularly to the use of novel members of the transcription enhancer factor TEF-1 family to regulate the transcription of cardiac specific genes.

BACKGROUND OF THE INVENTION

Genes may be regulated at the transcriptional level by cis-acting regulatory elements such as promoters and enhancers, and by trans-acting factors that bind to promoters and enhancers. Promoter elements are typically located within approximately 200 nucleotides of the gene transcription initiation site. Enhancer elements, first discovered in DNA tumor viruses, may be located several hundred or thousand bases upstream or downstream of the transcription initiation site, may function in either orientation, and are often preferentially or exclusively tissue-specific.

Comparisons of the sequences of promoters and enhancers reveal that certain sequence motifs may be found in classes of regulatory elements, and that genes that are regulated by these cis-acting elements may themselves be functionally related. That is, promoter and enhancers having related sequence motifs may exhibit commonalities of regulation.

An example of this commonality of regulation is the relationship between the regulatory elements of genes involved in skeletal muscle determination genes, including MyoD, myf5, myogenin, and herculin (the MyoD family of muscle specific trans factors), reviewed in Ordahl, C., *Curr. Topics in Dev. Biol.* (1992) 145–168. The members of the myoD family bind an MEF-1 sequence motif found in many skeletal muscle specific genes, for example creatine kinase and skeletal fast troponin I.

A major family of muscle-specific promoter elements are the M-CAT sequence motifs, which are variants of a canonical sequence 5'-CATTCCT-3' (SEQ ID NO:1), see Thompson W. R. et al., *J. Biol. Chem.* (1992) 266: 22678–22688, Shimizu, N. et al. *Mol. Cell Biol.* (1992) 12: 619–630, Flink I. L. et al., (1992) *J. Biol. Chem.* 267: 9917–9924, Parmacek M. S. et al., *Mol. Cell. Biol.* (1992) 12: 1967–1976, and Davidson, L et al., *Cell* (1988) 54: 931–942. M-CAT elements were first identified in the cardiac troponin T gene, Mar and Ordahl, *J.Cell. Biol.* (1988) 107: 573–585, and Mar and Ordahl, *Mol. Cell. Biol.* (1990) 10: 4271–4283. The M-CAT elements govern transcription from numerous gene promoters in both cardiac and in skeletal muscle.

A family of trans-acting regulatory factors are the TEA domain proteins which share a conserved DNA binding domain and are transcription factors that govern developmental functions in a wide variety of animal and plant phyla, Burglin, T. R. et al., *Cell* (1991) 66: 11–12, and Andrianopoulos, A., et al. *Plant Cell* (1991) 3: 747–748. TEA domain proteins include scalloped which regulates lineage progression in Drosophila sensory neuronal development, ABAA of *Asperaillus nidulans*, a developmental pathway gene required for the differentiation of asexual spores, and yeast TEC1 which is involved in transcriptional activation of the transposon Ty1. The human TEA homologue is TEF-1 (transcription enhancer factor-1), a cellular-encoded factor used by SV40 and papillomavirus-16 to activate their gene expression, Davidson L et al., *Cell* (1988) 54: 931–942.

A human NTEF-1 CDNA has been cloned from HeLa cells, Xiao J. H. et al., *Cell* (1991) 65: 551–568. In addition, the mouse homolog has been cloned from PCC4 embryonal carcinoma cells, Blatt C. et al., *Nucleic Acids Research* (1993) 21(3): 647–748. TEF-1 is highly enriched in the nuclei of striated muscle cells, Farrance I. K. G. et al., *J. Biol. Chem.* (1992) 267(24): 17234–17240. Despite the knowledge of the sequence of human NTEF-1, its cellular role and implication in muscle and cardiac gene regulation remains unknown.

Myocardial hypertrophy, an increase in the mass of the heart, occurs in many common cardiovascular dysfunctions, including hypertension, myocardial infarction, valve disease, and cardiomyopathy. Although the hypertrophic response may be a mechanism for maintaining cardiac pump function in response to hemodynamic challenges, hypertrophy is also associated with disorders of excitation, relaxation, and contraction. Ventricular hypertrophy is associated with significant increase in morbidity and mortality in hypertension, Simpson P. C. et al., *Mol. Cell. Biochem.* (1991) 104: 35–43. The hypertrophic phenotype is related to the differentiation state of the cell. Adult cardiac cells are maintained in a post-mitotic state. However, in certain cardiac dysfunctions, such as hypertrophy, these cells exhibit an embryonic or fetal differentiation state. In other dysfunctions, e.g. cardiac tumors, the cells dedifferentiate and proliferate. Thus, it would be desirable to regulate genes involved in the establishment and maintenance of cardiac cellular differentiation. The present invention fulfills these and other needs.

SUMMARY OF THE INVENTION

In accordance with the present invention, DNA sequences encoding avian TEF-1 have been isolated and sequenced. The present invention provides novel TEF-1 family gene products which provide differential transcriptional regulation of genes ("target genes") having naturally occurring or recombinant heterologous TEF-1 binding sites, including cardiac genes. In one embodiment, nucleic acids in the form of expression constructs are provided comprising one or more sequences that encode DTEF-1 isoforms that can be used for transcriptional regulation of target genes. The constructs can be used for producing large amounts of the DTEF-1 isoforms or fragments thereof, including antisense products thereof, for determining the regions of DTEF-1 used to regulate cardiac genes, for providing mutated analogs of DTEF-1, for identifying cofactors and coactivators of DTEF-1 activity which may be involved in muscle and other gene transcription and targets of therapeutic intervention, and for evaluating drugs for their physiological activity in cardiac dysfunction. In other embodiments, the invention provides methods of modulating DTEF-1 activity by the transcription, translation, processing or modification of DTEF-1.

The present invention provides a purified and isolated recombinant nucleic acid comprising at least about 25 contiguous nucleotides which encodes a DTEF-1 polypeptide. DTEF-1A and DTEF-1B isoform nucleic acids and polypeptides are specifically provided. Usually, the encoded segment is at least about 20 amino acids, and is preferably capable of binding a TEF-1 binding site.

The present invention also encompasses cells transfected with the DTEF-1 nucleic acids and expression constructs, typically where the cell is a eukaryotic cell.

In another aspect of the invention, the DTEF-1 genes and proteins of the present invention may be used to intercede in cardiac dysfunctions, including cardiac hypertrophy.

BRIEF DESCRIPTION OF THE DRAWINGS

FIGS. 1(a)-1(d) show the nucleic acid sequence (SEQ ID NO:2) and deduced protein sequence (SEQ ID NO:3) of avian RTEF-1A. The nucleotide sequence includes bases 1–1627. The deduced amino acid sequence of RTEF-1A comprises amino acids 1–432. The protein sequence commences with the amino acid leucine, encoded by nucleotides TTG at positions 185–187 of the nucleotide sequence.

FIGS. 2(a)-2(d) show the nucleic acid sequence (SEQ ID NO:4) and deduced protein sequence of avian RTEF-1B (SEQ ID NO:5). The nucleotide sequence includes bases 1–1666. The deduced amino acid sequence of RTEF-1B comprises amino acids 1–445. The protein sequence commences with the amino acid leucine, encoded by nucleotides TTG at positions 185–187 of the nucleotide sequence. The sequence includes 39 nucleotide bases (corresponding to the 13 underlined amino acid residues), which represent the alternatively spliced exon in RTEF-1B.

FIG. 3 shows the deduced amino acid sequence of TEF-1 family gene products. The alignment of avian RTEF-1A (SEQ ID NO:2) from its leucine translation initiator with human NTEF-1 (hNTEF-1) (SEQ ID NO:6) from its iso-leucine translation initiator. Amino acids in hNTEF-1 identical to those in chicken RTEF-1A are shown by dots. Dashes indicated gaps introduced to maintain alignment. The TEA binding domains are boxed, and the position of the RTEF-1B and RTEF-1C specific sequences, at Lys$^{117}$ and Pro$^{195}$ of the avian RTEF-1A sequence. respectively, are indicated by diamonds. The additional amino acids present in RTEF-1B are KTQVDKYDFSSEK (SEQ ID NO:7). The additional amino acids present in RTEF-1C are VCL.

FIGS. 5A, 5B, 5BB, 6C and 5D show the structure and encoded amino acid sequences of DTEF-1 cDNAs. FIG. 5A is a schematic of the DTEF-1A and 1B isoforms. Small open boxes indicate non-coding sequence; large boxes indicate coding sequence; alternatively spliced 1A and 1B exons are indicated. Black boxes indicate TEA domain. FIGS. 5B and 5BB show the nucleotide (SEQ ID NO:18) and deduced amino acid sequence (SEQ ID NO:19) of DTEF-1A. AUA and AUG initiators in the context of their putative respective Kozak sequences are underlined. Asterisk indicates stop codon; the TEA domain is doubly underlined. The 3' poly-adenylation signal is in bold face. FIG. 5C shows a comparison of the amino acid sequence of TEA domains of chick/human NTEF-1 (SEQ ID NO:22), chick RTEF-1 (SEQ ID NO:23), drosophila scalloped (sd) (SEQ ID NO:24) and DTEF-1A (SEQ ID NO:25) and 1B (SEQ ID NO:26). Amino acid sequences of TEA domains (central separated portion) and immediate flanking residues are shown. Dots indicate identity. FIG. 5D shows the nucleotide and derived amino acid sequence for alternatively spliced segments of DTEF-1A (SEQ ID NO:27 and 28) and DTEF-1B (SEQ ID NO:29 and 30). Boldface text indicates residues that constitute the 3' end and carboxy terminal of the TEA domain. Underlined regions represent nucleotide and amino acid differences between DTEF-1A and DTEF-1B. The DTEF-1B alternative splicing domain results in predicted polypeptide sequence one amino acid shorter than that predicted for DTEF-1A.

DESCRIPTION OF THE PREFERRED EMBODIMENT

Figure 5A:
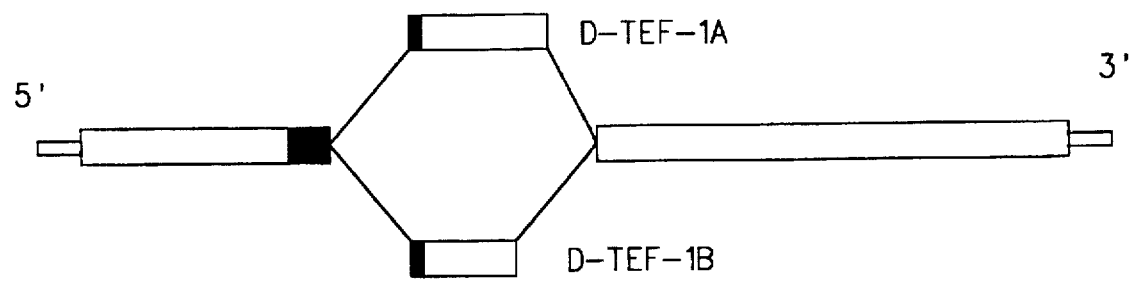

In view of our recent identification of two new TEF-1 family members (RTEF-1 and DTEF-1) we propose a system of nomenclature for the known TEF-1 related genes in vertebrates (Table 1). This system is based on the first cloned vertebrate TEF-1 family member, human TEF-1 (Xiao, J. H. et al., *Cell* (1991) 65: 551–568). The avian, rat and murine homologues of human TEF-1 are grouped in the NTEF-1 or nominal TEF-1 class (Xiao, J. H. et al., *Cell* (1991) 65: 551–568, Blatt, C. et al., *Nucleic Acids Res.* (1993) 21: 747–748) based on their high degree of homology (97% at the amino acid level, see Table 1). Another closely related class of TEF-1 cDNAs/genes, RTEF-1 (Related to NTEF-1) has been identified in chick (Stewart, A. F. et al. *J. Biol. Chem.* (1994) 269: 3147-3150) and mouse, sharing higher amino acid sequence homology to each other (89%) than to the NTEF-1 class (74%). The DTEF-1 (Divergent TEF-1) class of TEF-1 genes includes cDNA products (DTEF-1A) which contain amino acid substitutions in the TEA domain (FIG. 5C) not found in any other published vertebrate TEF-1 TEA domain thus defining its divergence.

TABLE 1

| PROPOSED NOMENCLATURE FOR VERTEBRATE TEF-1-RELATED GENES | | | | |
|---|---|---|---|---|
| Proposed Class Name | Former Names | % Identity within Class | % Identity to Human TEF-1 | Ref. |
| NTEF-1 | human TEF-1 | 97 | 100 | 15 |
| | rat TEF-1 | | 99 | # |
| | mouse TEF-1 | | 99 | 27 |
| | chick NTEF-1 | | 97 | * |

TABLE 1-continued

PROPOSED NOMENCLATURE FOR VERTEBRATE TEF-1-RELATED GENES

| Proposed Class Name | Former Names | % Identity within Class | % Identity to Human TEF-1 | Ref. |
|---|---|---|---|---|
| RTEF-1 | chick TEF-1A,B,C,D | 89 | 76 | 25 |
|  | mouse TEF-1 |  | 77 | # |
| DTEF-1 | chick DTEF-1A,B |  | 72 | * |
| ETEF-1 | mouse ETF-1 | 98 | 67 | 30 |
|  | rat c-TEF |  | 67 | # |

Percent identity figures within members of a single class and compared to human NTEF-1, which is set arbitrarily at 100%.
Symbols
15 Xiao, J. H. et al., Cell (1991) 65: 551–568
25 Stewart, A. F. et al. J. Biol. Chem. (1994) 269: 3147–3150
27 Blatt, C. et al., Nucleic Acids Res. (1993) 21: 747–748
30 Yasunami, M. et al., J. Biol. Chem. (1995) 270: 18649–18654
*described herein
personal communication Generally, the nomenclature used hereinafter, the laboratory procedures in cell culture, molecular genetics, and nucleic acid chemistry and hybridization described below are those well known and commonly employed in the art. Standard techniques are used for recombinant nucleic acid methods, polynucleotide synthesis, and cell culture. Generally, enzymatic reactions, oligonucleotide synthesis and purification steps are performed according to the manufacturer's specifications. The techniques and procedures are generally performed according to the conventional methods in the art and various general references which are provided throughout this document. The procedures therein are believed to be well known in the art and are provided for the convenience of the reader.

As used herein, "nucleic acid" refers to a deoxyribonucleotide or ribonucleotide polymer in either single- or double-stranded form, and unless otherwise limited, would encompass known analogs of natural nucleotides that can function in a similar manner as naturally occurring nucleotides.

Except where otherwise indicated, where reference to nucleic acid base numbering is made, that reference uses the transcription initiation site as +1, with all downstream (3') sequences being numbered sequentially thereafter. Upstream sequences 5' of the transcription initiation site are numbered commencing at −1, with each upstream base being numbered sequentially thereafter. Thus for example, a promoter element labelled as having position −268 is 268 nucleotides 5' (or upstream) of the transcription initiation site of that gene.

A nucleic acid is "operably linked" when placed into a functional relationship with another nucleic acid sequence. For instance, a promoter or enhancer is "operably linked" to a coding sequence if the promoter causes the transcription of the sequence. Generally, operably linked means that the DNA sequences being linked are contiguous and, where necessary to join two protein coding regions, contiguous and in reading frame.

The term "encoding" refers generally to the sequence information being present in a translatable form, usually operably linked to a promoter. An anti-sense strand is considered to also encode the sequence, since the same informational content is present in a readily accessible form, especially when linked to a sequence which promotes expression of the sense strand. The information is convertible using the standard, or a modified, version of the genetic code. See e.g. Watson et al., (1987) Molecular Biology of the Gene, 4th Edition, Benjamin, Menlo Park, Calif.

The term "isolated" as applied to nucleic acid means a nucleic acid, for example, an RNA, DNA, or mixed polymer molecule which is substantially separated from other DNA sequences which naturally accompany a native sequence, e.g. ribosomes, polymerases, and many other genome sequences. The term includes a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. An isolated nucleic acid will generally be a homogenous composition of molecules, but will in some embodiments, contain minor heterogeneities. This heterogeneity is typically found at the polymer ends or at portions not critical to a desired biological function or activity.

The term "recombinant" refers to a nucleic acid sequence which is not naturally occurring, or is made by the artificial combination of two or more otherwise separated segments of sequence. This artificial combination is often accomplished by either chemical synthesis means, or by the artificial manipulation of isolated segments of nucleic acids, e.g. by genetic engineering techniques, which are standard in the art. Restriction enzyme recognition site are often the target of such artificial manipulations, but other site specific targets, e.g. promoters, DNA replication sites, regulation sequences, control sequences, or other useful features may be incorporated by design. A similar concept is intended for recombinant polypeptide, for example fusion polypeptides or chemically synthesized polypeptides.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified in the laboratory is naturally-occurring.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

A polypeptide fragment, or segment, is a stretch of amino acid residues of at least about 3 amino acids, usually at least about 9 amino acids, more usually at least about 13 amino acids, and in various embodiments, at least about 20 or more amino acids. In a nucleic acid, a fragment or segment is a stretch of at least about 6 nucleotides, often at least about 9 nucleotides, usually at least about 12 nucleotides, typically at least about 18 nucleotides, more typically at least about 21 nucleotides, and in various preferred embodiments, at least about 24 or more nucleotides.

The human homolog of NTEF-1 binds to the GT-IIC (5'-CATTCCA'3' (SEQ ID NO:8)), Sph-I (5'-CATGCTT-3' (SEQ ID NO:9)), and Sph-II (5'-CATACTT-3'(SEQ ID NO:10)) binding sites in SV40 virus, and activates transcription from the SV40 early promoter. It is also believed to mediate large T antigen activation of the SV40 late promoter by a direct interaction between NTEF-1 and large T antigen, Hwang J.-J. et al., *EMBO J.* (1993) 12(6) 2337–2348. NTEF-1 contains a DNA binding domain termed the TEA domain. Although NTEF-1 is found in non-muscle tissue, it is highly enriched in the nuclei of striated muscle cells.

Due to the cellular specificity of TEF-1 transcriptional activation, localized coactivators (or transcription intermediatory factors, TIF'S) are believed to be involved in TEF-1 mediated transcriptional regulation. Thus, in addition to the TEA DNA binding domain, the TEF-1 protein contains activation sites, which are sites of interactions with cofactors and activators that augment cell-specific regulatory and differentiation mechanisms.

According to the present invention, TEF-1 gene family polypeptides are provided, which are capable of regulating transcription of target genes containing TEF-1 binding sites, and in particular, regulating the transcription of cardiac target genes. In a specific embodiment, nucleic acids and polypeptides encoding DTEF-1A and DTEF-1B isoforms are provided. The nucleotide sequence of avian DTEF-1A and DTEF-1B are designated as SEQ ID NO: 18 and SEQ ID NO:20, respectively. The corresponding amino acid sequence of avian DTEF-1A and DTEF-1B are designated as SEQ ID NO:19 and SEQ ID NO:21, respectively. The DTEF-1 nucleic acids and constructs can comprise all or part of the sequence of either SEQ ID NO:18 or SEQ ID NO:20. The DTEF-1 polypeptides may comprise the entire or part of the amino acid sequence of SEQ ID NO:19 or SEQ ID NO:21. DTEF-1 fusion proteins are also included.

The DTEF-1 compounds and compositions have varied uses. The isolation of new TEF-1 gene family members, DTEF-1A and DTEF-1B, is important as a starting point to investigate the role of DTEF-1 isoforms in the development and differentiation of muscle, particularly cardiac muscle. In one aspect, cardiac muscle gene promoters dependent on DTEF-1 can now be identified. The DTEF-1 isoform DNAs and polypeptides provide the tools for these investigations. Elucidation of DTEF-1 mediated transcriptional regulation of cardiac muscle development may yield approaches to treating cardiac dysfunction such as cardiac hypertrophy. The expression of target cardiac muscle genes can be controlled by modifying DTEF-1 activity to increase or decrease transcription as appropriate, from DTEF-1 responsive promoters. The DTEF-1 genes and proteins as well as DTEF-1 dependent promoters are all potential targets for modulating DTEF-1 activity.

In view of the aforementioned, full length DTEF-1 isoform cDNAs are useful to prepare expression constructs from which large amounts of DTEF-1 polypeptides or fragments thereof can be conveniently produced in in vitro cell culture. The availability of sufficient amounts of DTEF-1 polypeptides will facilitate the production of DTEF-1 isoform specific antibodies and the biochemical characterization of the DTEF-1 proteins.

As used herein, the term "TEF-1" comprises all gene family polypeptides and isoforms and analogs of TEF-1 which have TEF-1 biological activity. As used herein, "TEF-1 binding sites" includes nucleic acid sequence elements or motifs which bind TEF-1 products, including the M-CAT, GT-IIC, Sph, and PKC sequence elements or fragments, analogs, or homologs thereof. TEF-1 binding sites may be present in nucleic acid sequences which are viral, prokaryotic, or eukaryotic in origin. The target genes for use in the invention may be any gene having naturally occurring TEF-1 binding or recognition sites, or a target which has been manipulated by recombinant DNA methodology to have TEF-1 binding sites operably linked to the target gene.

In some embodiments of the invention, the regulation of target genes may be modulated by methods which alter the TEF-1 mRNA or protein. These methods include altering the transcription, translation, splicing, processing and export of TEF-1 MRNA species. Other methods include altering the intracellular localization of the TEF-1 mRNA. Yet further methods include manipulation of the cellular translation mechanisms to exploit the non-methionine start codon of TEF-1. In yet further methods, post-translational modifications or alterations of the intracellular locations of the TEF-1 proteins may be made. In other methods, alterations in the TEF-1 protein may be made to modulate its activity with cofactors or TIFs. In other embodiments, endogenous TEF-1 dependent gene expression may be modulated through the administration of small molecules, drugs, peptides, growth factors, nucleic acids, macromolecules, radiation, radiant energy or other non-invasive or invasive measures.

The TEF-1 polypeptides and analogs thereof of the invention include full length natural forms, fragments of the natural forms, fusion proteins generated with the natural forms or fragments thereof, and multi-protein complexes including TEF-1 or fragments thereof. The present invention also provides for biologically active TEF-1 polypeptide fragments, including organic molecules or peptidomimetics which simulate peptide interactions, as described for example, in Fauchere, *J. Adv. Drug Res.* (1986) 15: 29; Veber et al. *TINS* (1985) p.392; and Evans et al. *J. Med. Chem* (1987) 30: 1229. Significant biological activities include binding to nucleic acid sequences containing TEF-1 binding sites, binding to specific cofactors or TIFs, enhancement and regulation of transcription, and other biological activities characteristic of TEF-1 polypeptides.

A human NTEF-1 cDNA was used to isolate TEF-1 avian cDNA's. Two full length TEF-1 homologs, RTEF-1A and RTEF-1B were isolated. The nucleotide (SEQ ID NO:2) and deduced amino acid sequence (SEQ ID NO:3) of RTEF-1A is shown in FIG. 1. The nucleotide sequence of RTEF-1A comprises nucleotides 1–1627, and the deduced amino acid sequence comprises residues 1 –432. The nucleotide (SEQ ID NO:4) and deduced amino acid sequence (SEQ ID NO:5) of RTEF-1B are shown in FIG. 2. The RTEF-1B sequence comprises nucleotides 1–1666, and the deduced amino acid sequence comprises residues 1–445.

Although human NTEF-1 is reported to have a translation initiation at an isoleucine residue, the TEF-1 polypeptides described herein have putative translation initiations at the leucine residue indicated by the trinucleotide TTG at positions 185–187 of the nucleotide sequence of FIGS. 1 and 2. The translation initiation codon observed in most eukaryotic proteins is methionine. This alternate translation regime may be a target for therapeutic intervention specific to TEF-1 with minor effects on the translation of other cellular proteins. The RTEF-1B amino acid sequence includes an additional 13 amino acids, KTQVDKYDFSSEK (SEQ ID NO:7). Potential protein phosphorylation sites are the threonine and the second occurrence of serine of this sequence.

The derived amino acid sequence of avian RTEF-1A is highly related to human NTEF-1, as shown in FIG. 3, with a 76% identical overall sequence, and 100% identity in the TEA domain, $Asp^{37}$ to $Lys^{108}$, shown boxed in FIG. 3. Two regions of divergence between RTEF-1 and human NTEF-1 are seen in the acidic N-terminal domain ($Thr^9$ to $Asn^{36}$) and in the proline-rich domain ($Pro^{150}$ to $Pro^{210}$) carboxy-terminal to the TEA domain. Despite the overall divergence, the acidic and proline-rich characters of these domains are retained in chicken RTEF-1A compared to human NTEF-1: 6 versus 7 acidic residues are conserved in the N-terminal and 13 versus 16 proline residues are conserved in the proline rich domain. These regions are two components of at least three interdependent transactivation domains in human NTEF-1, Hwang J. -J. et al., *EMBO J.* (1993) 12: 2337–2348, so that the conservation of the acidic and proline rich character of these domains may reflect a species-independent conservation of function.

Figure 4:
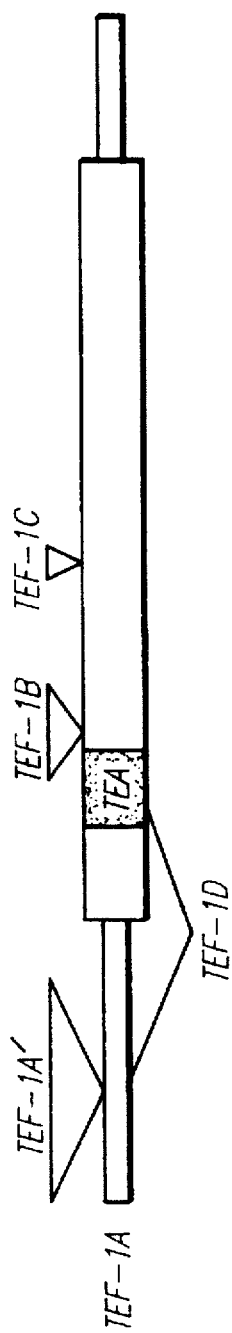
FIG. 4 is a schematic diagram of five TEF-1 splicing variants obtained by PCR cloning. RTEF-1A is diagrammed with inserts (shown as triangles above the sequence) at nucleotide 155 (RTEF-1A'), at nucleotide 585 (RTEF-1B) and at nucleotide 769 (RTEF-1C). The fourth variant has a deletion from nucleotide 155 to nucleotide 407 (RTEF-1D), shown as a triangle below the sequence. The small open boxes indicate 5' and 3' untranslated sequences and the large open box indicates the coding sequence, with the TEA domain filled.

RTEF-1B is a novel isoform containing an extra stretch of 13 amino acids, KTQVDKYDFSSEK (SEQ ID NO:7), carboxy-terminal to the TEA domain, between Lys$^{117}$ and Asp$^{118}$ that is believed to arise from alternative splicing of the RTEF-1 pre-MRNA, and shown diagrammatically in FIG. 4. The RTEF-1B exon is highly charged (7 of 13 residues) and contains two potential protein kinase C phosphorylation sites, at threonine and the second occurrence of serine at positions 2 and 11 respectively, of the 13 amino acid insert of RTEF-1B.

In addition to RTEF-1A and RTEF-1B, PCR cloning analysis revealed three other alternatively spliced isoforms, as shown in FIG. 4. One of these, RTEF-1A', corresponds to a variant of human NTEF-1 that is alternatively spliced in the 5' untranslated region, Xiao, J. H. et al., supra. The variant RTEF-1C is identical to RTEF-1A except for the presence of an alternative exon of 9 nucleotides between Pro$^{195}$ and Gly$^{196}$, as shown in FIG. 4. The RTEF-1C isoform has only been observed in cardiac tissue, and thus is potentially very useful in therapeutic applications specific to cardiac tissue. The RTEF-1C specific exon is "VCL". A third isoform, RTEF-1D, lacks a major portion of the TEA domain, and thus may be defective in DNA binding. The RTEF-1D isoform may thus have therapeutic utility as it may encode a dominant negative modulator of the bioactivity of other TEF-1 polypeptides or cofactors. RTEF-1A and RTEF-1B were the most abundant clones obtained and were present in all tissues examined, as were RTEF-1A' and RTEF-1D.

RTEF-1 MRNA is enriched in chicken cardiac and skeletal muscle tissue. Substantially lower levels are present in liver and gizzard, and RTEF-1 MRNA is barely detectable in brain. This distribution corresponds well to that of MCBF as determined by gel shift assay, Mar, J. H. et al. *Mol. Cell. Biol.* (1990) 10: 4271–4283, and southwestern blotting, Farrance I. K. G. et al. *J. Biol. Chem.* (1992) 267: 17234–17240. The predominant size of chicken RTEF-1 mRNA is approximately 1.7 kb. Less abundant RTEF-1 transcripts at 3.5 kb, 8 kb and 12 kb may represent partially processed primary transcript. In contrast, the mouse NTEF-1 mRNA is 10 kb, Blatt, C. et al., supra, and the human NTEF-1 transcript in HeLa cells is 12 kb in length, with minor species of 2.4 to 3.5 kb, as described in Xiao, J. H. et al., supra. The large size of mammalian NTEF-1 mRNA is probably due to the presence of a long 3' untranslated region lacking a clear polyadenylation consensus signal. The chicken RTEF-1 cDNAs have a very short 3' untranslated region (128 bp) and a clear polyadenylation consensus followed by a polyA tract.

M-CAT binding elements and M-CAT binding factor (MCBF) are implicated in a variety of genes that show cardiac-specific transcription, for example cardiac troponin T, cardiac troponin C, skeletal α-actin, β-myosin heavy chain, α-myosin heavy chain, genes that show skeletal muscle specific transcription, for example, β-acetylcholine receptor, and genes that show vascular smooth muscle specific transcription, including smooth muscle α-actin. Examples and locations of M-CAT binding elements found in promoters and enhancers of genes having cardiac-specific regulation or expression are provided in Table 2.

TABLE 2

| Gene | M-CAT | Position | |
|---|---|---|---|
| Cardiac Troponin T | CATTCCT | –95 to –89 | (SEQ ID NO:1) |
|  | CATTCCT | –72 to –66 | (SEQ ID NO:1) |
| Cardiac Troponin C | CATTCCC | –50 to –56 | (SEQ ID NO:11) |
| Skeletal α-Actin | CATTCCT | –66 to –60 | (SEQ ID NO:1) |
| β-Myosin Heavy Chain | | | |
| human | CATTCCA | –284 to –290 | (SEQ ID NO:8) |
| rabbit | CATTCCA | –264 to –270 | (SEQ ID NO:8) |
| rat | CATTCCA | –274 to –280 | (SEQ ID NO:8) |
|  | CATACCA | –210 to –204 | (SEQ ID NO:12) |
| α-Myosin Heavy Chain | CATTCCT | –230 to –236 | (SEQ ID NO:1) |

RTEF-1A and RTEF-1B encoded polypeptides have the same DNA binding specificity as native MCBF. A gel shift mobility assay showed that binding of in vitro translated RTEF-1A and RTEF-1B to MCAT and GT-IIC containing oligomers was competed by wild type M-CAT DNA but not by DNA containing a mutant M-CAT motif. Thus, TEF-1 encoded isoproteins are M-CAT binding factors.

Direct analysis of human NTEF-1 transactivating functions has proven difficult because transfected human NTEF-1 inhibits expression of GT-IIC driven reporter constructs in HeLa cells, which contain endogenous TEF-1. Furthermore, transfected NTEF-1 is not active in cell lines lacking endogenous TEF-1. Thus, NTEF-1 has been proposed to require limiting, cell specific co-activators for its function. On the other hand, NTEF-1 activation function could be demonstrated in HeLa cells using vectors expressing GAL4/NTEF-1 chimeras transfected at low ratios of expression vector to GAL-4 dependent reporter.

Thus, to determine whether the chicken RTEF-1 isoforms are capable of differential activation of transcription in muscle and non-muscle cells, chimeras were constructed in which RTEF-1A and RTEF-1B, lacking the TEA and N-terminal domains, were fused to the DNA binding domain of GAL4. These fusion constructs were then cotransfected into cultured embryonic skeletal muscle and fibroblast cells with a GAL-4 dependent CAT reporter gene. The chimera of the RTEF-1A isoform did not activate in this context. However, the RTEF-1B chimera activated basal transcription of the reporter 3- to 6- fold in both muscle and fibroblast cells. A similar result was seen using the quail embryonic muscle cell line QM7 described in Antin P. B. et al., *Dev. Biol.* (1991) 143: 111–121, and by using a different GAL4 responsive reporter in primary quail muscle cells. Lack of transactivation by the RTEF-1 chimeras was not due to lack of expression since the levels of both chimeras was shown to be approximately equal by immunoprecipitation with anti-GAL4 and anti-TEF-1 antibodies. Thus, the alternative exon of RTEF-1B, containing thirteen amino acids, confers a transactivation capacity that is lacking in RTEF-1A. Its function is not affected by the truncation and chimerism of the protein and is active in mesodermal cells.

The isoforms of the present invention permit cellular manipulation of TEF-1 to regulate the transcription of genes that contain regulatory sequences bound by TEF-1 family members or analogs thereof. Regulatory sequences to which TEF-1 binds include M-CAT binding sequences, GT-IIC binding sequences, and protein-kinase C response elements (5'TGTGGTATG-3'), as described in Kariya K. et al., *J. Biol. Chem.* (1993) 268 (35):26658–26662.

Protein kinase C (PKC) is a family of phospholipid dependent serine threonine kinases present in all cells. PKC mediated phosphorylation is believed to be important in transcriptional regulation. Kariya K. et al., *J. Biol. Chem.* (1993) 268 (35): 26658–26662. More specifically, βPKC plays a role in transcriptional regulation in cardiac myocytes, through its involvement in the a1 adrenergic receptor signal transduction pathway. Simpson, P. C. *Mol. Cell. Biochem.* (1991) 104: 35–43.

Thus, TEF-1, by virtue of its ability to bind DNA sequence motifs including M-CAT, GT-IIC, and PKC elements, may be used to modulate transcription of any gene operably linked to that TEF-1 binding site, whether such gene is naturally linked to the binding site or whether a recombinant gene containing the TEF-1 binding site is generated. TEF-1 may be used to modulate the transcriptional activity from the target gene. Modulation comprises up-regulation, namely increased levels of transcription, as well as down-regulation, namely decreased levels of transcription.

A suitable target gene for transcriptional modulation is the cardiac troponin T (cTNT) gene. cTNT encodes a cardiac protein which is also expressed transiently during skeletal muscle development. The upstream regulatory elements of the cTNT gene are described in U.S. Pat. No. 5,266,488, the contents of which are hereby incorporated by reference. A 67 nucleotide sequence upstream of the cardiac TNT gene, between positions −268 and −201 contains DNA sequences which are required for efficient expression of the cardiac TNT promoter in embryonic cardiac cells. The cardiac TNT regulatory region includes two MCAT binding sequence motifs at positions −95 to −89 and at −72 to −66. Therefore, TEF-1 family members may bind to and modulate the transcriptional activity of cTNT. A preferred expression cassette for cardiac regulation of cTNT by TEF-1 contains the cTNT coding region, and 101 bases of upstream cTNT promoter sequence, including two TEF-1 binding sites, namely M-CAT elements, as described in U.S. Pat. No. 5,266,488.

In some embodiments of the invention, the transcription of cellular genes operably linked to TEF-1 binding sites may be indirectly modulated by the modification of the endogenous TEF-1 in the cell. Modification of endogenous TEF-1 may occur by a variety of methods, including altering the transcription, translation, processing, stability or biological activity of TEF-1.

The transcriptional regulation of cardiac genes may be modulated by altering the rate of synthesis or rate of turnover of the TEF-1 MRNA, to provide a non-native amount of mRNA. Suitable approaches for altering the rate of synthesis or turnover include altering the rate of transcription of the TEF-1 promoter, altering the rate of processing of the TEF-1 primary transcript, altering the rate of export of TEF-1 primary transcript, or altering the cytoplasmic localization or stability of the TEF-1 transcript. In one embodiment, the transcription rate of DTEF-1 mRNA is modified by mutations in the form of deletions, insertions or nucleotide substitutions in the DTEF-1 promoter sequences or any other sequences necessary for transcription of the particular isoform. The gene can also be deleted entirely such as by homologous recombination using gene targeting techniques (see, e.g., Capecchi, *Science*, 244:1288–1292 (1989).

The translation initiation of TEF-1 may be altered to exploit the non-methionine start site of TEF-1. Without intended to be limited by any particular theory, it is believed that translation initiation at methionine codons requires a specific initiator tRNA, N-formyl-methionyl-tRNA. An analogous translation initiator is believed to permit translation from non-methionine start codons. Thus, the presence or absence of translation initiators specific for proteins which have non-methionine residues at their N-terminus, such as RTEF-1 and DTEF-1A and -1B may serve to modulate the translation rate and cellular specificity of these proteins.

Similarly, the TEF-1 protein level may be altered by changing the rate of turnover of the TEF-1 protein product. Suitable methods include differentially affecting the alternative splicing of TEF-1, by cotranslation of TEF-1 with other factors, by nuclear localization of the TEF-1 protein, or by differential translation of alternative TEF-1 mRNA's. The transcription rate of TEF-1 will indirectly affect the level of its protein synthesis.

In another embodiment of the invention, the biological activity of the endogenous TEF-1 protein product may be altered. Suitable methods for altering the biological activity of the protein include altering the DNA binding and/or activating capability of the protein, altering the relative balance of the isoforms, altering interactions between TEF-1 and other proteins, and by altering the post-translational modification of TEF-1. In a preferred embodiment, the DNA binding capability of the TEF-1 protein is altered by mutations in the TEA domain.

In one aspect of the invention, the biological activity of TEF-1 may be modulated by the creation, deletion, or alteration of a TEF-1 DNA binding site in a target gene such as a cardiac gene. Cardiac troponin T or troponin C genes in particular are suitable targets. In a particular embodiment, a TEF-1 DNA binding site specific for binding by a DTEF-1 isoform and present in a cardiac target gene, is modified.

In another aspect of the invention, the TEF-1 DNA binding site may be rendered unavailable for TEF-1 binding by the addition of a antagonist ligand that binds to the DNA binding site of the target gene but fails to have an effect on transcriptional regulation of the target gene. Such an antagonist ligand includes a peptide corresponding to the DNA binding domain or TEA domain of a TEF-1 protein or a polypeptide containing such a domain sequence. Another example of an antagonist ligand is a recombinant TEF-1 polypeptide wherein the transcription activation sites of the protein are modified such as by mutagenesis, to modulate its activation ability. The recombinant polypeptide can be a fusion protein. A specific embodiment provides for a modified DTEF-1 polypeptide, polypeptide fragment or fusion protein that binds a TEF-1 binding site of a DTEF-1 dependent promoter but fails to activate transcription.

Alternatively, the ligand may alter TEF-1 activity by preventing binding of TEF-1 to TEF-1 binding sites. For example, an oligonucleotide containing the sequence of the TEF-1 binding site of a target gene can be used to inhibit binding of a particular TEF-1 to the target gene.

The biological activity of a TEF-1 protein can also be altered to increase the rate of transcription of its target gene. The TEF-1 protein may be altered in the DNA binding domain to increase its binding affinity for the target gene or the activation sites may be altered to increase the efficiency of activation.

In some embodiments, interaction between TEF-1 and its cellular coactivator or cofactor molecules may be altered to modulate transcriptional regulation of a target gene by TEF-1. For example, molecules which mimic or interact with interactive surfaces on TEF-1 or its cofactors may be used to modulate the TEF-1 cofactor interaction. These molecules could be specific to TEF-1 family members, or could interact with a sequence of TEF-1 common to all forms of TEF-1.

TEF-1 and fragments thereof may also be post-translationally modified by pharmaceutical agents or by other means in order to modulate transcription in target genes. Post translational modifications include glycosylation, phosphorylation, acetylation, methylation, ubiquitination, disulfide bond formation, and other post-translational modifications. The novel amino acid residues in the alternative exons of the RTEF-1 isoforms described herein, for example, the 13 amino acids of the RTEF-1B isoform, contain phosphorylation sites. The role of phosphorylation in cellular signal transduction is described in Bruce Alberts et al. *Molecular Biology of the Cell*, 2nd Edition, (1989) Garland Publishing Inc., New York, the contents of which are hereby incorporated by reference. Phosphorylation can be blocked eg. by mutating the phosphorylated residues.

In another embodiment of the invention, TEF-1 cofactors may be affected to modify the expression of TEF-1-regulated genes. TEF-1 may require specific coactivator molecules for activity, Xiao, J. H. et al., supra. These proteins may be potential targets for therapies that will affect TEF-1 activity. In some embodiments, these therapies may be designed against TEF-1 alternative exons, and thus against TEF-1 isoforms such as RTEF-1B.

In another embodiment of the invention, exogenous TEF-1 or TEF-1 cofactors may be administered locally or systemically to provide localized effects of TEF-1. TEF-1 activity in muscle is dependent on tissue specific coactivators or binding cofactors. Thus, TEF-1 could be systemically administered but still exhibit tissue specific expression and function. Similarly, knockouts, modifications, additions, or alterations of TEF-1 genes or its co-factors in specific tissues may provide regulation of TEF-1 and TEF-1 dependent activity in those tissues.

The compositions of the present invention may be used to regulate cardiac gene sequences in a tissue specific manner. Thus, the genes and proteins, and fragments thereof, of the present invention may be used to intercede in a wide variety of cardiac dysfunctions, including cardiomyopathy. As used herein, cardiomyopathy (or cardiac myopathy) includes any structural or functional abnormality of the ventricular myocardium, valvular disease, systemic or pulmonary vascular disease, isolated pericardial, nodal, or conduction system disease, or epicardial coronary artery disease, as described in, for example, the *Merck Manual*, 16th Edition, Merck & Co., Rahway N.J., the contents of which hereby incorporated by reference.

The nucleic acid compositions of this invention will generally be in RNA, DNA or mixed polymer forms. The described DNA embodiments are usually derived from genomic DNA or CDNA, prepared by synthesis, or derived from combinations thereof. The DNA compositions generally include the complete coding region encoding TEF-1 or fragments thereof, e.g. comprising at least 3 codons (9 bases), usually at least 10 codons (30 bases), more usually about 13 codons (39 bases), typically about 20 codons (60 bases), more typically about 30 codons (90 bases) and in some embodiments, even more.

The novel nucleic acids provided herein are useful for producing RTEF-1 and DTEF-1 isoforms. The DNA fragment or portions thereof will be used to prepare an expression construct for a RTEF-1 or DTEF-1 protein. The expression construct normally comprises one or more DNA sequences encoding a TEF-1 under the control of a native or other promoter. When more than one sequence encoding TEF-1 is present in the construct, the sequence may encode the same or different forms of TEF-1. Usually the promoter will be a eukaryotic promoter for expression in a eukaryotic cell, preferably a mammalian or avian cell. The transcriptional regulatory sequences for the expression of TEF-1 will typically include a heterologous promoter enhancer or promoter which is recognized by the host. The selection of an appropriate promoter will depend upon the host, as described, for example, in Sambrook et al., *Molecular Cloning*, 2nd Edition, Cold Spring Harbor Laboratory, Cold Spring Harbor, N.Y. Conveniently available expression vectors which include the replication system and transcriptional and translational regulatory sequences together with an insertion site for the TEF-1 DNA sequence may be employed. Examples of workable combinations of cell lines and expression vectors are described in Sambrook et al. In some circumstances, an inducible promoter may be preferred.

Where it is desired to produce the TEF-1 proteins or fragments thereof in a prokaryotic host, a preferred promoter is a prokaryotic promoter, e.g. trp, lac, and lambda, and others described in Sambrook et al. Usually a strong promoter will be employed to provide high level of transcription and expression.

The expression construct will often be contained in a vector capable of stable extrachromosomal maintenance in an appropriate cellular host or may be integrated into the host genome. The expression construct may be bordered by sequences which allow for insertion into a host, such as transposon sequences, lysogenic viral sequences, or the like. Normally, markers are provided with the expression construct which allow for selection of host cells containing the construct. The marker may be on the same or a different DNA molecule, preferably on the same DNA molecule.

In mammalian and avian cells, the TEF-1 gene itself may provide a convenient marker. In prokaryotic cells, markers such as a resistance to a cytotoxic agent, complementation of an auxotrophic host to prototrophy, production of a detectable product and the like, may be more convenient.

The expression construct may be joined to a replication system recognized by the intended host cell. Various replication systems include viral replication systems such a retroviruses, simian virus, bovine papilloma virus, baculovirus, and the like. In addition, the construction may be joined to an amplifiable gene, to generate multiple copies of the TEF-1 gene.

The means of introducing the expression construct into the host cell will vary depending on the particular construction and the target host. Introduction can be achieved by any convenient means including fusion, conjugation, transfection, transduction, electroporation, injection or the like, as are known to those of skill in the art, and described in, for example, Sambrook supra. Introduction of constructions encoding TEF-1 polypeptides is also contemplated. The host cells will normally be immortalized cells, i.e. cells that can be continuously passaged in culture. Generally, these cells will be mammalian or avian cell lines able to express TEF-1, and where appropriate, splice and process the TEF-1 transcript to produce the desired isoform.

A wide variety of hosts, both prokaryotic and eukaryotic, will be employed for expression of the present TEF-1 polypeptides. Useful hosts include bacteria such as *E. coli*, yeast, filamentous fungi, insect cells, mammalian and avian cells, typically immortalized e.g. various murine, avian, human, monkey, and Chinese hamster ovary cell lines or derivatives thereof. In some cases, the cells may be derived from a neoplastic host cell or wild type cells transformed with oncogenes, tumor causing viruses or the like.

The TEF-1 or anti-TEF-1 containing compositions of the present invention may be used to increase or decrease cardiac hypertrophies. Hypertrophy is a primary or secondary lesion in many clinical cardiac conditions. Hypertrophy may be decreased or prevented by the application of the TEF-1 products of the invention, and thus modulating this principal regulator of cardiac sarcomeric and other target gene promoters, and the known target of hypertrophic signal pathways. TEF-1 thus has utility in diagnosis, treatment, and prevention of left chamber hypertrophy such as hypertrophic obstructive cardiomyopathy (or idiopathic hypertrophic subaortic stenosis), congenital bicuspid aortic valve stenosis, subaortic stenosis, in which antihypertrophic therapy would have an additional secondary therapeutic effect in prevention of the reoccurrence of the resected membranes), and left and right chamber hypertrophic conditions such as in tetrology of fallot pulmonary stenosis.

The TEF-1 sequences of the invention may be used to increase hypertrophy in conditions where such increase would be desirable, for example to increase the power of a weakened heart in dilated cardiomyopathy, or chronic low level rejection of transplanted hearts.

The TEF-1 containing compositions may also be used to affect the differentiation state of cardiac cells, for example, cardiac tumors. Cardiac cells exist in a post-mitotic state. Cardiac hypertrophy changes the differentiation state of cardiac cells, and hypertrophied cells exhibit fetal or embryonic cellular differentiation patterns. Similarly, cancer cells exhibit altered differentiation states, whereby the cells are dedifferentiated, and proliferate. TEF-1, as a differentiation factor, may be capable of causing these cells to re-undergo terminal differentiation, and cease proliferating, thus providing useful treatment or prevention of cardiac tumors. In other embodiments, portions of cardiac tissues are damaged irreversibly after ischemic damage, for example, infarcted heart tissue. The cells may become despecified to no longer exhibit the cardiac muscle phenotype. In this embodiment of the invention, the heart tissue could be repaired by the introduction of new cardiac myoblasts or stem cells, respecified from other tissue by the introduction of TEF-1 and its cofactors or coactivators.

The presence of TEF-1 in non-cardiac cells indicates that it may be manipulated to regulate transcription in noncardiac tissues. For example, RTEF-1 and genes having RTEF-1 binding sites are found in skeletal muscle, smooth muscle, and skin tissues, as well as in very early embryos. Use of the compositions of the invention in skeletal muscle includes intervention in gene regulation related to repair of damaged muscle, hypertrophy, drug delivery, and dieting or anorexia. Injured muscle cells exhibit an embryonic differentiation phenotype, such that cardiac muscle isoforms of the sarcomeric proteins are re-expressed. Thus, the use of TEF-1 to directly or indirectly induce these isoforms may assist in the repair of damaged muscle, and when administered prophylactically, may prevent the damage from occurring or may lessen the severity of the damage. TEF-1 can also be used to induce mild hypertrophy in skeletal muscle cells or to directly or indirectly induce cardiac isoforms of sarcomeric proteins. This has particular utility for the treatment or prevention of conditions of muscle atrophy, such as following prolonged bed rest, inactivity of a muscle group, or prolonged exposure to zero gravity conditions. In dieting and in eating disorders such as anorexia, muscle loss may be experienced. Usually, adipose tissue rather than muscle is preferentially regained after the return to a normal diet. TEF-1 has utility in these instances for restimulating sarcomeric protein production in skeletal muscle to encourage the formation of muscle rather than adipose tissue.

The TEF-1 compositions of the present invention have particular utility when co-introduced with engineered genes, such as for use in gene therapy. For example, gene therapy for muscular dystrophy may comprise administration of dystrophin, but a strong muscle specific promoter would be required, such as one having multiple TEF-1 binding sites. Thus, the administration of a TEF-1 family polypeptide to increase transcriptional activation in genes with cis-acting TEF-1 binding sites has use in gene therapy and in drug delivery applications.

The compositions of the present invention also have use for co-introduction with gene therapy or drug delivery for smooth muscle. Proliferation of vascular smooth muscle is an important component of stenosis and restenosis of blood vessels. TEF-1 may be used to influence the contractile or proliferative phenotypic state of smooth muscle. Vascular smooth muscle is thus a target for the introduction of engineered genes, particularly for blood borne proteins such as clotting factors, but a strong muscle promoter would be required, such as one having multiple TEF-1 binding sites. Thus, the administration of a TEF-1 family polypeptide to increase transcriptional activation in genes with cis-acting TEF-1 binding sites finds use in smooth muscle applications.

The compositions containing the compounds of the invention can be administered for prophylactic and or therapeutic applications. In therapeutic applications, compositions are administered to a patient already suffering from a disease or dysfunction, as described above, in an amount sufficient to cure, ameliorate, or at least partially arrest the symptoms of the dysfunction or disease and its complications. An amount adequate to accomplish this is defined as a "therapeutically effective dose".

In prophylactic applications, compositions containing the compounds of the invention are administered to a patient susceptible to or otherwise at risk for a particular dysfunction. Such an amount is defined to be a "prophylactically effective dose".

The active ingredients of the present invention will typically be administered together with a pharmaceutically acceptable carrier. Pharmaceutically acceptable carriers will include water, saline, buffers, and other compounds described, e.g., in the *Merck Index*, Merck & Co., Rahway, N.J. See, also, *Bioreversible Carriers in Drug Design, Theory and Application*, Roche (ed.), Pergamon Press, (1987).

The quantities of reagents and active ingredient necessary for prophylaxis or therapy will depend on a variety of factors including the dysfunction to be treated, means and route of administration, the target site of the active ingredient, the physiological state of the patient, and other drugs being administered. Thus, treatment dosages should be titrated to optimize safety and efficacy. Optimization of dose is within the purview of the skilled artisan. Typically, dosages used in vitro may provide useful guidance in the amounts useful for in situ administration of these reagents and active ingredients. Animal testing of effective doses for treatment of particular cardiac disorders will provide further predictive indication of human dosage. Generally, dosage levels of between 0.001 to 10 mg/kg of body weight daily are administered for effective therapeutic or prophylactic dosage. Considerations and methods for administration are described in, for example, Gilman et al. (eds) Goodman and Gilman's: *The Pharmacological Basis of Therapeutics*, 8th Edition, Pergamon Press, and *Remington's Pharmaceutical Sciences* 18th Edition, 1990, Mack Publishing Co, Easton, Pa., each of which is hereby incorporated by reference. Suitable methods for administration include oral, intravenous, intraperitoneal, intramuscular, iontophoretic, and transdermal administration.

The active ingredient of the invention can be administered orally in solid dosage forms, such as capsules, tablets, and powders, or in liquid dosage forms, such as elixirs, syrups, and suspensions; it can also be administered parenterally in sterile liquid dosage forms. The active ingredient may also be administered intravenously as nanoparticles or colloid drug delivery system, or in liposomes. Gelatin capsules contain the active ingredient and as inactive ingredients powdered carriers, such as glucose, lactose, sucrose, mannitol, starch, cellulose or cellulose derivatives, magnesium stearate, stearic acid, sodium saccharin, talcum, magnesium carbonate and the like, as are described in the *Merck Index*, Merck & Co. Rahway, N.J. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The invention will now be further illustrated by Examples 1 through 8 which are exemplary and not scope-limiting.

EXPERIMENTAL EXAMPLES

Example 1 cDNA library Screening and PCR cloning of RTEF-1

The EcoRI/BglII fragment of human NTEF-1 cDNA pXJ40RTEF-1A, Xiao, J. H. et al., supra, was used to screen a chicken fetal day-11 skeletal muscle cDNA library (Stratagene), and a day-12 whole chick cDNA library (Clontech, Palo Alto, Calif.), from which partial clones were obtained. These clones were used to obtain clones RTEF-1A and RTEF-1B from a day-3 embryonic chicken heart cDNA library (Stratagene). RACE-PCR (Frohman M. A. et al., *Proc. Nat. Acad. Sci.* (1988) 85: 8998–9002) of fetal day-12 skeletal muscle cDNA confirmed the 5' sequence of RTEF-1B. cDNA was synthesized from RNA of liver, gizzard, heart and skeletal muscle, and was used with sequence specific primers to generate PCR products which were cloned into the T/A vector available from Invitrogen. All clones were sequenced on both strands by dideoxy sequencing using sequence-specific oligonucleotides.

Example 2

In Vitro translation and gel mobility shift assay

RTEF-1A and RTEF-1B cDNA's coding from $Ser^{16}$ to the carboxy terminus were ligated in frame to the PRSET vector available from Invitrogen. In vitro transcription and translation were done according to manufacturer's instructions (Promega, Madison, Wis.). Mobility shift polyacrylamide gel electrophoresis using the procedure of Farrance I. K. G. et al., *J. Biol. Chem.* (199) 267: 17234–17240, was performed on 5 µl of in vitro translated protein and 1 µg poly(dI-dC), exception that the acrylamide:bis (44:1) concentration was 6%. The sequence of the mutant oligonucleotide was 5'-TCGGGTGTTGGGTACCTCTCTGC-3' (SEQ ID NO:13), annealed to 5'-CCGAGCAGAGAGGTACCCAACAC-3' (SEQ ID NO:14).

Example 3

GAL4-TEF1 Chimera studies

Chimeric (fusion) expression vectors were constructed in the plasmid pGAL4mpolyII, Webster, H. J. G. et al., *Cell* (1988) 54: 199–207. The entire carboxy terminus of RTEF-1A or RTEF-1B isoforms from $Val^{101}$ was fused to the DNA binding domain of GAL4 (amino acids 1–147). These chimeric expression vectors were cotransfected with 2 µg of a GAL4-dependent CAT reporter, (17 merx2) βglobinCAT (Webster, H. J. G., supra) into cultured embryonic chicken breast muscle or fibroblast cells by standard calcium phosphate transfection methods. Cells were cultured on 60 mm dishes as described in Mar J. H. et al. *J. Cell Biol.* (1988) 107: 573–585. CAT reporter activities were measured by the CAT diffusion assay described in Sambrook et al., *Molecular Cloning: A laboratory Manual*, 2nd Edition, Cold Spring Harbor Laboratory Press, Cold Spring Harbor, N.Y.

Example 4

Immunoprecipitation of nuclear extracts.

Primary cultures of chick embryo muscle cells on 10 cm dishes were transfected with 20 ng each of GAL4/RTEF-1A, GAL4/RTEF-1B, and GAL4DBD. Eighteen hours later the cells were labelled for six hours with 200 µCi of $^{35}S$-translabel (ICN), in 3 mls of methionine/cysteine-free medium. After labelling, nuclear extracts were prepared as described in Farrance I. K. G. et al., *J. Biol. Chem.* (1992), supra, with the following modifications. After washing with relaxation buffers I and II, cells were incubated for ten minutes in lysis buffer (50 mM Tris/MES pH 7.8), 1 mM DTT, 0.1% TritonX-100) and scraped into 1 ml of lysis buffer, incubated for 10 minutes on ice, and then Dounced for 20 strokes. Nuclei were spun out at 190×g for five minutes and extracted on ice for 30 minutes in 0.4M NaCl. Supernatant was collected after a ten minute, 13,000 rpm centrifugation at 4° C. in a microfuge and incorporated cpm's were determined. After preclearing the extracts with protein A agarose (Gibco BRL, Gaithersburg, Md.), equal cpms ($3 \times 10^6$) were immunoprecipitated with anti-TEF-1, anti Gal-4 antibodies or non-immune serum in RIPA buffer lacking SDS and protein A agarose as described in Harlow E. et al. *Antibodies: A laboratory manual* (1988) Cold Spring Harbor Laboratory Press, Cold Spring Harbor, N.Y.

Example 5

Comparison of TEF-1-related cDNAs isolated from chicken.

To determine the possible number of TEF-1-related genes, chicken cDNA, RTEF-1A, was used to screen chicken cDNA libraries under low stringency hybridization conditions to isolate both closely and distantly related cDNAs. The nucleotide sequence of a number of cDNA clones revealed three classes of cDNAs. The nucleotide sequence and conceptual translated amino acid sequence of one class of cDNA clones were identical to those of the RTEF-1A probe. A major portion of that amino acid sequence (cRTEF-1A) is provided as SEQ ID NO:17.

A second class of cDNAs, designated GL2/3/5 was found to encode proteins with an amino acid sequence that was more closely related to that of human NTEF-1 (hNTEF-1; SEQ ID NO:15) as in Xiao et al. (1991), supra.) when compared to the human NTEF-1 sequence. The amino acid sequence of GL2/3/5 SEQ ID NO:16 has far fewer substitutions than RTEF-1A when compared to the human NTEF-1 sequence. These data strongly indicate that GL2/3/5 is the chicken homologue of the published human NTEF-1 gene.

From the above set of experiments, it was concluded that RTEF-1A is a product of a new and different gene, one that is related to, but distinct from, the published human NTEF-1 gene. TEF-1A mRNAs are expressed in many tissues but are enriched in both cardiac and skeletal muscle. Our experiments further indicated that RTEF-1 proteins are components of a muscle-specific complex that binds to promoter control elements (M-CAT motifs). Isoproteins encoded by RTEF-1A and 1B cDNAs are bonafide M-CAT binding factors (MCBF). RTEF-1B, at least, can activate transcription when linked to a heterologous DNA binding domain. Thus, RTEF-1A may be the important player in the control of muscle specific, notably cardiac and skeletal muscle specific, transcriptional regulation.

Muscle tissues contain at least three MCBF complexes on electrophoretic mobility shift assays, one of which appears to be muscle-specific and upregulated upon differentiation. All muscle MCBF complexes contain TEF-1 proteins, but only one complex contains proteins encoded by TEF-1 cDNAs isolated thus far. Additional TEF-1-related cDNAs might, therefore, account for the multiple MCBF complexes found in muscle and non-muscle tissues. Examples 6 to 8 below describes the identification of a new, divergent class of TEA domain gene that we name DTEF-1. DTEF-1 is a sequence specific M-CAT binding factor whose mRNA is enriched in cardiac but not skeletal muscle or most non-muscle tissues. Thus, DTEF-1 may be involved in the cardiac-specific regulation of M-CAT-dependent promoters.

Example 6

PCR cloning and cDNA library screening for DTEF-1

Complementary DNA synthesized from chick retina RNA was used for PCR amplification of TEF-1 cDNA products using the following primers: sense, 5'-TGG AGT/C CCN GAT/C ATT/C AGA A/GCA-3' (SEQ ID NO:31); antisense, 5'-ATC ATA/G TAT/C TCA/G CAC ATG/T/C GG-3'(SEQ ID NO:32). The PCR reaction was conducted in an automated thermal cycler for 35 cycles under the following conditions; 1 min at 94° C., 1 min 30 sec at 55° C., 1 min 30 sec at 72° C. A 900 b.p. fragment was isolated and used to screen an adult chick heart cDNA library (from Clonetech). Five TEF-1 cDNAs were isolated, and one of these was used to screen a seven week chick heart cDNA library (1×10$^6$ recombinants, Stratagene) under reduced stringency conditions (40% formamide, 40° C., 5× SSC, 5× Denhardts, 0.1% SDS, 100 μg/ml salmon sperm DNA). Clones were sequenced on both strands using the Sequenase kit (USB) or a dideoxy Taq DNA sequencer (Applied Biosystems).

Example 7

Northern blot analysis

Total RNA from embryonic day 12 chick tissues was isolated using standard methods (Chomczynski, P. et al., *Anal. Biochem.* (1987) 162: 156–159). Twenty five μg of total RNA was electrophoresed on a 0.8% agarose-1.1M formaldehyde gel and transferred to a Hybond N membrane (Amersham). Crosslinking, prehybridization and hybridization were as described by the manufacturer. A DTEF-1 specific probe was used for hybridization consisting of a 366 b.p. EcoRI-PvuII fragment (nt 1–nt 366) that was labeled by random priming (Rediprime, Amersham) with $^{32}$P dCTP (Amersham, 6000 Ci/mmol) to a specific activity of 109 cpm/μg. Membranes were hybridized for 18 hours and then washed at 42° C. with 2× SSC, 0.1% SDS, and at 65° C. with 1.1× SSC, 0.1% SDS prior to autoradiography. Ethidium bromide staining of the gel prior to transfer was used to verify the equivalence of total RNA loads.

Example 8

In vitro transcription/translation and gel mobility shift assay

The SmaI/EcoRI (nt 388 to 3' end) fragment of DTEF-1A was ligated in frame into PvuII/EcoRI digested and phoshatase-treated pRSET vector (Invitrogen). Linearized plasmids were transcribed with T7 RNA polymerase according to the manufacturer (Promega). One microgram of capped RNA was then translated in 20 μl reticulocyte lysates (Promega). Gel shifts were performed using 5 μl of in vitro translated protein, as previously described (Stewart, A. F. et al. *J. Biol. Chem.* (1994) 269: 3147–3150).

Results

Identification of multiple classes of TEF-1-related cDNAs. An adult chicken heart cDNA library was screened at low stringency using a TEF-1 CDNA probe. Four cDNA clones were isolated whose nucleotide sequence was determined to represent overlapping cDNA segments derived from one gene with higher amino acid homology to human TEF-1 (97% identity with human TEF-1) than to TEF-1-related cDNAs previously isolated from avian heart and skeletal muscle (Stewart, A. F. et al. *J. Biol. Chem.* (1994) 269: 3147–3150). Because the nucleotide differences between these two classes of cDNA were found throughout their length, we concluded that there are at least two TEA-domain genes within the avian genome. To preserve but extend the extant TEF nomenclature (Table 1), we designated those genes from mouse, rat, and chick most homologous to the human TEF-1 cloned from HeLa cells (Xiao, J. H. et al., *Cell* (1991) 65: 551–568, Blatt, C. et al., *Nucleic Acids Res.* (1993) 21: 747–748, Shimizu, N. et al., *Mol. Cell. Biol.* (1992) 12(2): 619–630) as NTEF-1 (Nominal TEF-1; that from which the name is derived). Since avian NTEF-1 was more related to human NTEF-1 than to our previously identified chick TEF-1-related cDNAs (96.5% vs. 76%; (Stewart, A. F. et al. *J. Biol. Chem.* (1994) 269: 3147–3150)), we redesignated these cDNAs and any homologous genes/cDNAs from other species as RTEF-1 (Related to TEF-1).

To identify further TEF-1-related genes, and in particular those that might be preferentially expressed during cardiac development, a partial avian NTEF-1 CDNA was used to screen a seven week chicken heart cDNA library under reduced stringency conditions. Of nine cDNA clones isolated, four had nucleotide sequences corresponding to RTEF-1. The nucleotide sequence of five other clones were divergent from that of either NTEF-1 or RTEF-1 (FIG. 5B) indicating that a third TEA-domain gene is present in the avian genome. We designate this new TEF-1-related gene DTEF-1 (divergent TEF-1) to indicate its higher degree of divergence from avian NTEF-1.

All five apparently full-length (1.9 kb) DTEF-1 cDNAs were identical except for a specific segment that suggests alternative splicing of the primary transcript of the DTEF-1 gene (FIG. 5A, 5D) generating predicted isoforms designated DTEF-1A and DTEF-1B. The deduced amino acid sequence of DTEF-1A (FIG. 5B) yields a 433 amino acid polypeptide that is 72% identical to both avian NTEF-1 and RTEF-1A.

The TEA domain is highly conserved throughout evolution and there is only a single amino acid change within this domain between the drosophila TEA domain gene scalloped and the human-, mouse- or chick-derived NTEF-1s; FIG. 5C). NTEF-1 and RTEF-1 are identical throughout their TEA domains. However, DTEF-1A, which represented four of the five cDNA clones, has two amino acid differences within the TEA domain as compared to NTEF-1 (FIG. 5C). Amino acid residue 87 of DTEF-1A contains a lysine instead of an arginine, and residue 94 contains a leucine in place of an isoleucine, preserving the basic and aliphatic natures, repectively, of the residues at these two positions.

The DTEF-1B isoform is identical to DTEF-1A at the nucleotide and amino acid levels except for an alternatively spliced 23 a.a. exon, extending from $Arg^{87}$ to $Gln^{109}$ (FIG. 5D) which replaces $Lys^{87}$ to $Lys^{110}$ and includes the last 10 amino acids of the TEA domain. The resultant TEA domain of DTEF-1B is identical to that of NTEF-1 (FIG. 5C).

Figure 6:
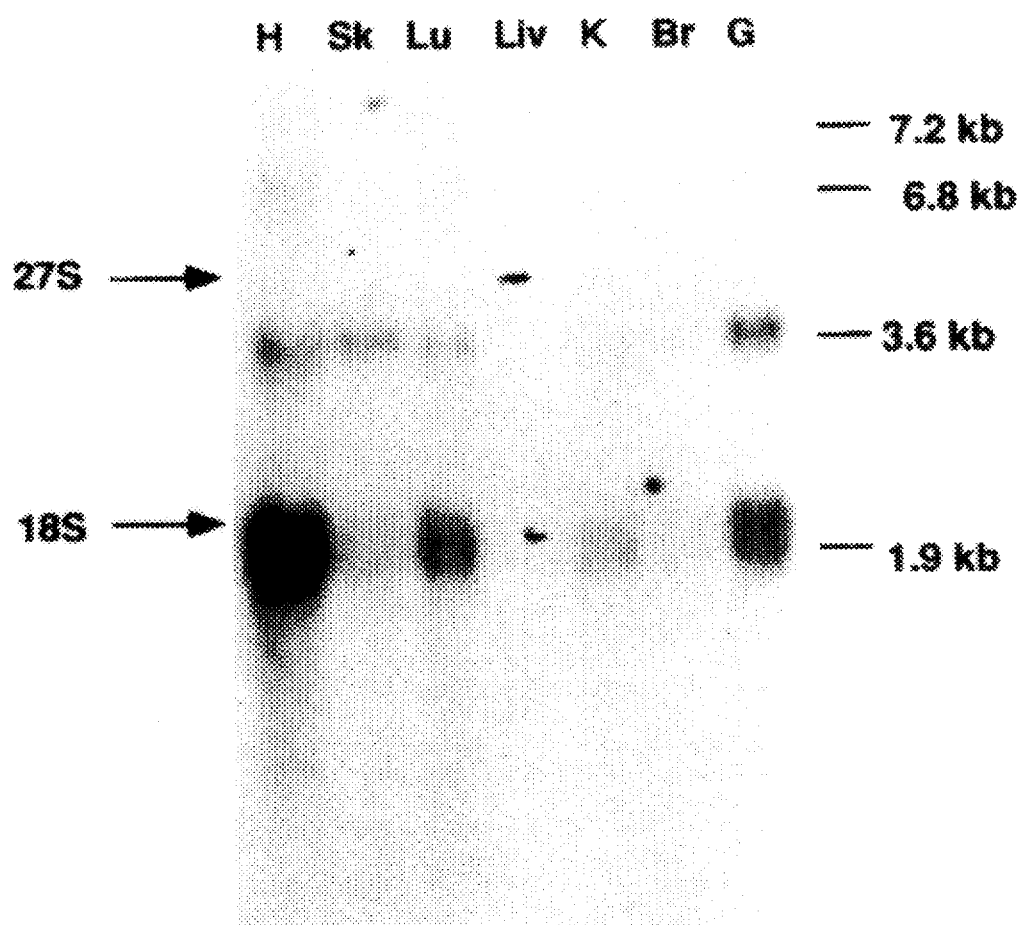
FIG. 6 shows a Northern blot analysis of DTEF-1 transcripts in embryonic day 12 chick tissues: Heart (H), skeletal (Sk), lung (Lu), liver (Liv), kidney (K), brain (Br), and gizzard (G). 18S and 27S ribosomal RNA mobilities are indicated.

Distribution of DTEF-1 transcripts in embryonic chick tissues. The distribution of DTEF-1 transcripts in embryonic chick tissues was examined by Northern blot analysis of total RNA using a DTEF-1 specific probe (FIG. 6). Four transcripts were detected; a predominant 1.9 kb transcript and minor 3.6 kb, 6.8 kb and 7.2 kb transcripts (6.8 and 7.2 kb transcripts appeared on longer exposures). These DTEF-1 transcripts are most abundant in cardiac muscle , and present at lower levels in lung, gizzard, and kidney (FIG. 6). DTEF-1 transcripts are present at trace levels, or absent, in skeletal muscle, liver and brain.

Figure 7:
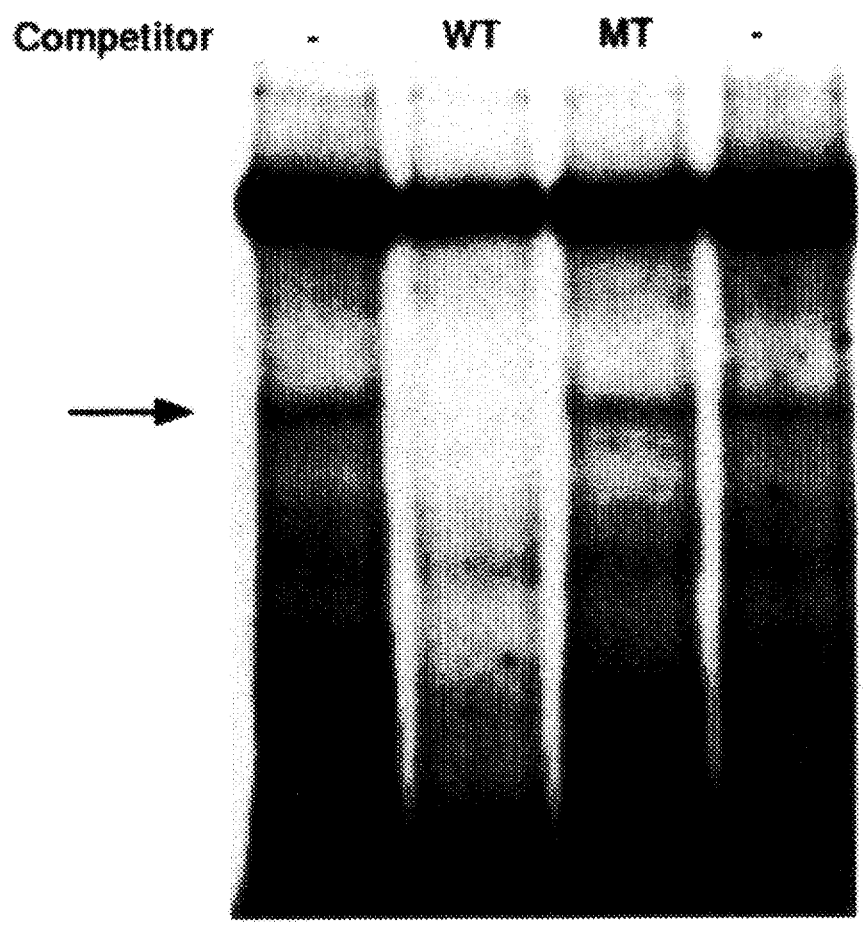
FIG. 7 is a gel showing that DTEF-1 encodes an M-CAT binding protein. DTEF-1A cDNA containing codons from Ser$^5$ to the C-terminus was used to produce in vitro transcribed mRNA that was translated in rabbit reticulocyte lysate. The in vitro translation of DTEF-1 fusion protein yielded a minority of full length protein. DTEF-1 fusion protein was incubated with radiolabeled M-CAT DNA and analyzed by electrophoretic mobility shift assay. Bands shown are the gel shift complexes formed with full length DTEF-1. Lane 1 and lane 4: no competitor (−); lane 2: wildtype competitor DNA (WT); lane 3: mutant competitor DNA (MT).

Cloned DTEF-1 binds M-CAT sites in a sequence-specific fashion. Because of the considerable sequence conservation between the TEA domains of DTEF-1, RTEF-1 and NTEF-1 it was predicted that DTEF-1 would retain the ability to form sequence-specific interactions with M-CAT elements. The DNA binding activity of in vitro translated DTEF-1A protein was tested using gel retardation assays. Full length DTEF-1A fusion protein bound to radiolabeled M-CAT probe producing a gel shift complex in the appropriate mobility range (FIG. 7, lanes 1 and 4). Moreover, this binding is sequence-specific since the presence of excess wildtype M-CAT DNA (FIG. 7, lane 2) competed effectively for binding, while mutant M-CAT competitor (FIG. 7, lane 3) did not. Thus, DTEF-1A is a bona fide M-CAT binding factor.

Vertebrate TEF-1 comprises a multigene family. NTEF-1 appears to be expressed in various tissues including heart, skeletal muscle, lung, kidney, brain and gizzard. RTEF-1 is also present in muscle tissue and one isoform can potentially transactivate muscle promoters through binding to M-CAT motifs (Stewart, A. F. et al. *J. Biol. Chem.* (1994) 269: 3147–3150). DTEF-1 is the newest and most divergent class of TEF-1-related cDNAs. Unlike NTEF-1 and RTEF-1, the expression of DTEF-1 is restricted to a few tissues, including heart but not skeletal muscle.

Sequence analysis of the DTEF-1 5' end indicated no potential AUG start codon in a favorable Kozak setting. The first potential AUG (residue 428) initiator codon exists in a poor Kozak consensus sequence (7/13 nucleotides, underlined in FIG. 5B). Most other cloned TEF-1 cDNAs are believed to initiate translation at isoleucine residues (Xiao, J. H. et al., *Cell* (1991) 65: 551–568, Stewart, A. F. et al. *J. Biol. Chem.* (1994) 269: 3147–3150, Blatt, C. et al., *Nucleic Acids Res.* (1993) 21: 747–748) and a reasonably favourable Kozak consensus (10/13 nucleotide homology with the Kozak consensus sequence; underlined in FIG. 5B) is found at the isoleucine codon (AUA) beginning at nucleotide 352. This is followed by a predicted open reading frame of 433 amino acids consisting of a serine-rich N-terminus, followed by a basic highly conserved TEA domain, and then a proline-rich region. Based upon this conceptual translation we conclude that the DNA binding and transactivation motif pattern is grossly conserved through all classes of vertebrate TEF-1 cDNAs consistent with general conservation of function for this protein.

Two isoforms of DTEF-1 were isolated. The DTEF-1A isoform differs from DTEF-1B by insertion of a 69 nucleotide segment that includes the C-terminal portion of the TEA domain. In all other regions these isoforms are identical in nucleotide sequence indicating that they are products of a single alternatively spliced gene. The DTEF-1B TEA domain is identical to all other published vertebrate TEA domains except that of DTEF-1A (FIG. 6C). DTEF-1A, on the other hand represents the first divergent vertebrate TEA domain protein due to the presence of a lysine at position 87 where an arginine is in human-N, mouse-N, chick-N, chick-R, Drosophila, and Aspergillus TEA domains. Similarly all known TEA domain genes encode an isoleucine at position 94 except for chick DTEF-1A and Aspergillus abaA which code for a similarly aliphatic leucine at that position.

The divergent region of DTEF-1A encompasses the predicted third helix of the TEA DNA binding domain. This helix was shown to be important in sequence-specific recognition of SV40 M-CAT-like elements by human NTEF-1 but the first helix appeared to be the most important for sequence-specific DNA recognition (Hwang, J. J. et al., *Embo. J.* (1993) 12: 2337–2348).

NTEF-1 mRNA is widely expressed in human, mouse and chick tissues. RTEF-1 message is also widely expressed, but is highly enriched in skeletal and cardiac muscle, and less abundant in gizzard, brain and liver. By contrast, DTEF-1 transcripts are highly expressed in heart, with significantly lower levels of expression in lung, gizzard and kidney, and minimal or no expression in skeletal muscle and brain. The selective enrichment of DTEF-1 mRNA in heart and the demonstration that DTEF-1 is a sequence-specific M-CAT binding factor is indicative of a role for DTEF-1 in cardiac-specific muscle gene regulation different from the roles played by other TEF-1 family members.

M-CAT elements were first described in the cardiac-specific cTNT promoter and since then most characterized cardiac promoters have been found to contain one or more functional M-CAT elements. M-CAT elements in the promoters of the β-myosin heavy chain and α-skeletal actin genes have been shown to be required for induction by $\alpha_1$-adrenergic agonists and protein kinase C (PKC) (Kariya K. et al., *J. Biol. Chem.* (1993) 268: 26658–26662, Karnes, L. R. et al., *J. Biol. Chem.* (1995) 270, 410–417). Several candidate PKC sites can be identified in the derived amino acid sequence of DTEF-1, including residues 81, 86, 219, 329, and 398. These potential PKC sites are conserved in avian NTEF-1 and RTEF-1 and mammalian NTEF-1, consistent with evolutionary conservation of potentially important regulatory sites. Since DTEF-1 is abundantly expressed in heart it may be a target for this PKC regulation and a potential mediator of the $\alpha_1$-adrenergic hypertrophy response.

The foregoing description of the preferred embodiments of the present invention has been presented for purposes of illustration and description. They are not intended to be exhaustive or to limit the invention to the precise form disclosed, and many modifications and variations are possible in light of the above teaching.

All publications, patents, and patent applications herein are incorporated by reference to the same extent as if each individual publication or patent application was specifically and individually indicated to be incorporated by reference.

Such modifications and variations which may be apparent to a person skilled in the art are intended to be within the scope of this invention.

What is claimed is:

1. A purified and isolated recombinant nucleic acid which comprises the sequence of SEQ ID NO:18.

2. A purified and isolated recombinant nucleic acid which comprises the sequence of SEQ ID NO:20.

3. The nucleic acid of claim 1 or 2, wherein the nucleic acid is operably linked to a promoter.

4. A eukaryotic cell transformed with a recombinant nucleic acid encoding a polypeptide having the sequence set forth as SEQ ID NO:19 or SEQ ID NO:21.

5. The eukaryotic cell of claim 4, wherein the eukaryotic cell is a human cell.

* * * * *